(12) United States Patent
Collinson et al.

(10) Patent No.: US 10,076,594 B2
(45) Date of Patent: Sep. 18, 2018

(54) FLUIDIC CONNECTOR FOR NEGATIVE PRESSURE WOUND THERAPY

(71) Applicant: Smith & Nephew PLC, London (GB)

(72) Inventors: Sarah Jenny Collinson, Hull (GB); John Gowans, Hessle (GB); Philip Gowans, York (GB)

(73) Assignee: Smith & Nephew PLC, London (GB)

( * ) Notice: Subject to any disclaimer, the term of this patent is extended or adjusted under 35 U.S.C. 154(b) by 276 days.

(21) Appl. No.: 14/715,527

(22) Filed: May 18, 2015

(65) Prior Publication Data

US 2016/0339158 A1 Nov. 24, 2016

(51) Int. Cl.
*A61M 1/00* (2006.01)
*A61F 13/02* (2006.01)
*A61F 13/53* (2006.01)
*A61F 13/00* (2006.01)

(52) U.S. Cl.
CPC ..... *A61M 1/0086* (2014.02); *A61F 13/00068* (2013.01); *A61F 13/0206* (2013.01); *A61F 13/0216* (2013.01); *A61M 1/0088* (2013.01); *A61M 1/0052* (2014.02); *A61M 2205/7518* (2013.01); *A61M 2205/7536* (2013.01)

(58) Field of Classification Search
CPC ............ A61F 13/00068; A61F 13/0206; A61F 13/0216; A61M 1/0052; A61M 1/0086; A61M 1/0088; A61M 2205/7518; A61M 2205/7536; A61M 25/04
See application file for complete search history.

(56) References Cited

U.S. PATENT DOCUMENTS

| | | |
|---|---|---|
| 3,568,675 A | 3/1971 | Harvey |
| 3,972,328 A | 8/1976 | Chen |
| 4,605,399 A | 8/1986 | Weston et al. |
| 4,921,492 A | 5/1990 | Schultz |
| 4,969,880 A | 11/1990 | Zamierowski |
| 5,056,510 A | 10/1991 | Gilman |
| 5,100,396 A | 3/1992 | Zamierowski |
| 5,180,375 A | 1/1993 | Feibus |
| 5,238,732 A | 8/1993 | Krishnan |
| 5,261,893 A | 11/1993 | Zamierowski |
| 5,358,492 A | 10/1994 | Feibus |
| 5,527,293 A | 6/1996 | Zamierowski |

(Continued)

FOREIGN PATENT DOCUMENTS

| | | |
|---|---|---|
| AU | 674837 B2 | 1/1997 |
| DE | 34 43 101 | 5/1986 |

(Continued)

OTHER PUBLICATIONS

US 7,186,244, 03/2007, Hunt et al. (withdrawn)

(Continued)

*Primary Examiner* — Adam Marcetich
(74) *Attorney, Agent, or Firm* — Knobbe, Martens, Olson & Bear LLP

(57) ABSTRACT

Disclosed herein are several embodiments of a wound treatment apparatus employing a fluidic connector for negative pressure wound therapy and methods of using the same. Some embodiments are directed to improved fluidic connectors for connecting to a wound site, for example a fluidic connector including a reinforcement, and methods of using the same.

42 Claims, 33 Drawing Sheets

(56) References Cited

U.S. PATENT DOCUMENTS

| | | |
|---|---|---|
| 5,549,584 A | 8/1996 | Gross |
| 5,599,289 A | 2/1997 | Castellana |
| 5,636,643 A | 6/1997 | Argenta et al. |
| 5,645,081 A | 7/1997 | Argenta et al. |
| 5,678,564 A | 10/1997 | Lawrence et al. |
| 5,701,917 A | 12/1997 | Khouri |
| 5,707,499 A | 1/1998 | Joshi et al. |
| 5,759,570 A | 6/1998 | Arnold |
| 5,795,584 A | 8/1998 | Totakura et al. |
| 5,911,222 A | 6/1999 | Lawrence et al. |
| 6,071,267 A | 6/2000 | Zamierowski |
| 6,142,982 A | 11/2000 | Hunt et al. |
| 6,345,623 B1 | 2/2002 | Heaton et al. |
| 6,458,109 B1 | 10/2002 | Henley et al. |
| 6,626,891 B2 | 9/2003 | Ohmstede |
| 6,648,862 B2 | 11/2003 | Watson |
| 6,685,681 B2 | 2/2004 | Lockwood et al. |
| 6,752,794 B2 | 6/2004 | Lockwood et al. |
| 6,755,807 B2 | 6/2004 | Risk et al. |
| 6,855,135 B2 | 2/2005 | Lockwood et al. |
| 6,936,037 B2 | 8/2005 | Bubb |
| 6,942,650 B1 * | 9/2005 | Schultz ................ B01D 46/24 454/66 |
| 6,951,553 B2 | 10/2005 | Bubb et al. |
| 6,979,324 B2 | 12/2005 | Bybordi et al. |
| D515,701 S | 2/2006 | Horhota et al. |
| 7,004,915 B2 | 2/2006 | Boynton et al. |
| 7,070,584 B2 | 7/2006 | Johnson et al. |
| 7,108,683 B2 | 9/2006 | Zamierowski |
| 7,195,624 B2 | 3/2007 | Lockwood |
| 7,198,046 B1 | 4/2007 | Argenta et al. |
| 7,216,651 B2 | 5/2007 | Argenta et al. |
| 7,279,612 B1 | 10/2007 | Heaton et al. |
| 7,316,672 B1 | 1/2008 | Hunt et al. |
| 7,338,482 B2 | 3/2008 | Lockwood et al. |
| 7,361,184 B2 | 4/2008 | Joshi |
| 7,381,859 B2 | 6/2008 | Hunt et al. |
| 7,438,705 B2 | 10/2008 | Karpowicz et al. |
| 7,485,112 B2 | 2/2009 | Karpowicz et al. |
| 7,503,910 B2 | 3/2009 | Adahan |
| 7,524,315 B2 | 4/2009 | Blott et al. |
| 7,531,711 B2 | 5/2009 | Sigurjonsson et al. |
| 7,534,927 B2 | 5/2009 | Lockwood |
| 7,569,742 B2 | 8/2009 | Haggstrom et al. |
| 7,615,036 B2 | 11/2009 | Joshi et al. |
| 7,625,362 B2 | 12/2009 | Boehringer et al. |
| 7,645,269 B2 | 1/2010 | Zamierowski |
| 7,651,484 B2 | 1/2010 | Heaton et al. |
| 7,670,323 B2 | 3/2010 | Hunt et al. |
| 7,678,102 B1 | 3/2010 | Heaton |
| 7,686,785 B2 | 3/2010 | Boehringer et al. |
| 7,699,823 B2 | 4/2010 | Haggstrom et al. |
| 7,708,724 B2 | 5/2010 | Weston |
| 7,722,582 B2 | 5/2010 | Lina et al. |
| 7,759,537 B2 | 7/2010 | Bishop et al. |
| 7,759,539 B2 | 7/2010 | Shaw et al. |
| 7,775,998 B2 | 8/2010 | Riesinger |
| 7,779,625 B2 | 8/2010 | Joshi et al. |
| 7,794,438 B2 | 9/2010 | Henley et al. |
| 7,811,269 B2 | 10/2010 | Boynton et al. |
| 7,838,717 B2 | 11/2010 | Haggstrom et al. |
| 7,846,141 B2 | 12/2010 | Weston |
| 7,862,718 B2 | 1/2011 | Doyen et al. |
| 7,909,805 B2 | 3/2011 | Weston |
| 7,910,791 B2 | 3/2011 | Coffey |
| 7,922,703 B2 | 4/2011 | Riesinger |
| 7,964,766 B2 | 6/2011 | Blott et al. |
| 8,021,347 B2 | 9/2011 | Vitaris et al. |
| 8,062,272 B2 | 11/2011 | Weston |
| 8,062,331 B2 | 11/2011 | Zamierowski |
| 8,080,702 B2 | 12/2011 | Blott et al. |
| 8,083,712 B2 | 12/2011 | Biggie et al. |
| 8,118,794 B2 | 2/2012 | Weston |
| 8,133,211 B2 | 3/2012 | Cavanaugh, II et al. |
| 8,147,468 B2 | 4/2012 | Barta et al. |
| 8,148,595 B2 | 4/2012 | Robinson et al. |
| 8,152,785 B2 | 4/2012 | Vitaris |
| 8,158,844 B2 | 4/2012 | McNeil |
| 8,162,907 B2 | 4/2012 | Heagle |
| 8,168,848 B2 | 5/2012 | Lockwood et al. |
| 8,188,331 B2 | 5/2012 | Barta et al. |
| 8,202,261 B2 | 6/2012 | Kazala, Jr. et al. |
| 8,207,392 B2 | 6/2012 | Haggstrom et al. |
| 8,241,261 B2 | 8/2012 | Randolph et al. |
| 8,257,326 B2 | 9/2012 | Vitaris |
| 8,282,611 B2 | 10/2012 | Weston |
| 8,298,200 B2 | 10/2012 | Vess et al. |
| 8,303,552 B2 | 11/2012 | Weston |
| 8,372,049 B2 | 2/2013 | Jaeb et al. |
| 8,372,050 B2 | 2/2013 | Jaeb et al. |
| 8,376,972 B2 | 2/2013 | Fleischmann |
| 8,382,731 B2 | 2/2013 | Johannison |
| 8,398,614 B2 | 3/2013 | Blott et al. |
| D679,819 S | 4/2013 | Peron |
| D679,820 S | 4/2013 | Peron |
| 8,425,478 B2 | 4/2013 | Olson |
| 8,444,612 B2 | 5/2013 | Patel et al. |
| 8,449,509 B2 | 5/2013 | Weston |
| 8,460,255 B2 | 6/2013 | Joshi et al. |
| 8,535,296 B2 | 9/2013 | Blott et al. |
| 8,569,566 B2 | 10/2013 | Blott et al. |
| 8,628,505 B2 | 1/2014 | Weston |
| 8,641,691 B2 | 2/2014 | Fink |
| 8,715,256 B2 | 5/2014 | Greener |
| 8,734,410 B2 | 5/2014 | Hall et al. |
| 8,771,244 B2 | 7/2014 | Eckstein et al. |
| 8,784,392 B2 | 7/2014 | Vess et al. |
| 8,801,685 B2 | 8/2014 | Armstrong et al. |
| 8,808,274 B2 | 8/2014 | Hartwell |
| 8,814,842 B2 | 8/2014 | Coulthard et al. |
| D714,433 S | 9/2014 | Armstrong et al. |
| 8,834,451 B2 | 9/2014 | Blott et al. |
| 8,905,985 B2 | 12/2014 | Allen et al. |
| 8,951,235 B2 | 2/2015 | Allen et al. |
| 9,017,302 B2 | 4/2015 | Vitaris et al. |
| 9,050,398 B2 | 6/2015 | Armstrong et al. |
| 9,061,095 B2 | 6/2015 | Adie et al. |
| 9,084,845 B2 | 7/2015 | Adie et al. |
| D746,435 S | 12/2015 | Armstrong et al. |
| RE45,864 E | 1/2016 | Peron |
| 9,227,000 B2 | 1/2016 | Fink et al. |
| D755,980 S | 5/2016 | Jakobsen et al. |
| 9,327,065 B2 | 5/2016 | Alberti et al. |
| 9,474,654 B2 | 10/2016 | Heagle et al. |
| RE46,289 E | 1/2017 | Peron |
| 9,539,373 B2 | 1/2017 | Jones et al. |
| 2003/0050594 A1 * | 3/2003 | Zamierowski ...... A61M 1/0058 604/46 |
| 2005/0076921 A1 * | 4/2005 | Rozier .................. A61M 25/02 128/877 |
| 2005/0101940 A1 | 5/2005 | Radl et al. |
| 2006/0009744 A1 | 1/2006 | Edrman et al. |
| 2006/0079852 A1 | 4/2006 | Bubb et al. |
| 2006/0100586 A1 | 5/2006 | Karpowicz |
| 2007/0055209 A1 | 3/2007 | Patel et al. |
| 2007/0225663 A1 | 9/2007 | Watt et al. |
| 2008/0132821 A1 | 6/2008 | Propp et al. |
| 2008/0195017 A1 | 8/2008 | Robinson et al. |
| 2008/0271804 A1 * | 11/2008 | Biggie ................ A61M 1/0088 138/137 |
| 2008/0306456 A1 | 12/2008 | Riesinger |
| 2009/0012501 A1 | 1/2009 | Boehringer et al. |
| 2009/0124988 A1 | 5/2009 | Coulthard |
| 2009/0126103 A1 | 5/2009 | Dietrich et al. |
| 2009/0131892 A1 | 5/2009 | Karpowicz et al. |
| 2009/0157016 A1 | 6/2009 | Adahan |
| 2009/0177172 A1 * | 7/2009 | Wilkes ................ A61M 1/0023 604/305 |
| 2009/0227968 A1 | 9/2009 | Vess |
| 2009/0227969 A1 | 9/2009 | Jaeb et al. |
| 2009/0234306 A1 | 9/2009 | Vitaris |
| 2009/0234309 A1 | 9/2009 | Vitaris et al. |
| 2009/0240185 A1 | 9/2009 | Jaeb et al. |
| 2009/0264837 A1 | 10/2009 | Adahan |

(56) References Cited

U.S. PATENT DOCUMENTS

| | | |
|---|---|---|
| 2009/0293887 A1 | 12/2009 | Wilkes et al. |
| 2009/0299249 A1 | 12/2009 | Wilkes et al. |
| 2009/0299251 A1 | 12/2009 | Buan |
| 2009/0299255 A1 | 12/2009 | Kazala, Jr. et al. |
| 2009/0299257 A1 | 12/2009 | Long et al. |
| 2009/0299303 A1 | 12/2009 | Seegert |
| 2009/0299306 A1 | 12/2009 | Buan |
| 2009/0299308 A1 | 12/2009 | Kazala et al. |
| 2009/0299340 A1 | 12/2009 | Kazala et al. |
| 2010/0069850 A1 | 3/2010 | Fabo |
| 2010/0069885 A1 | 3/2010 | Stevenson et al. |
| 2010/0087767 A1* | 4/2010 | McNeil ............ A61M 1/0088 602/42 |
| 2010/0125258 A1 | 5/2010 | Coulthard et al. |
| 2010/0160880 A1 | 6/2010 | Weston |
| 2010/0160901 A1 | 6/2010 | Hu et al. |
| 2010/0185163 A1* | 7/2010 | Heagle ............ A61F 13/0203 604/290 |
| 2010/0268198 A1 | 10/2010 | Buan et al. |
| 2010/0305526 A1 | 12/2010 | Robinson et al. |
| 2010/0318052 A1 | 12/2010 | Ha et al. |
| 2010/0324510 A1 | 12/2010 | Andresen et al. |
| 2011/0004172 A1 | 1/2011 | Eckstein et al. |
| 2011/0009838 A1 | 1/2011 | Greener |
| 2011/0028918 A1 | 2/2011 | Hartwell |
| 2011/0118683 A1 | 5/2011 | Weston |
| 2011/0130712 A1 | 6/2011 | Topaz |
| 2011/0152800 A1* | 6/2011 | Eckstein ............ A61M 1/0088 604/319 |
| 2011/0184361 A1* | 7/2011 | Crojzat ............ A61M 1/0088 604/319 |
| 2011/0224631 A1 | 9/2011 | Simmons |
| 2011/0230849 A1* | 9/2011 | Coulthard ............ A61M 1/0088 604/319 |
| 2011/0282309 A1 | 11/2011 | Adie et al. |
| 2012/0041399 A1 | 2/2012 | Blott et al. |
| 2012/0116334 A1* | 5/2012 | Albert ............ A61F 13/02 604/319 |
| 2012/0302976 A1 | 11/2012 | Locke et al. |
| 2013/0066285 A1* | 3/2013 | Locke ............ A61F 13/00068 604/318 |
| 2013/0096519 A1 | 4/2013 | Blott et al. |
| 2013/0116635 A1 | 5/2013 | Fleischmann |
| 2013/0138054 A1 | 5/2013 | Fleischmann |
| 2013/0138060 A1 | 5/2013 | Haqqstrom et al. |
| 2013/0144230 A1 | 6/2013 | Wu et al. |
| 2013/0150814 A1 | 6/2013 | Buan |
| 2013/0165878 A1 | 6/2013 | Heagle |
| 2013/0172835 A1 | 7/2013 | Braga et al. |
| 2013/0267921 A1 | 10/2013 | Weston |
| 2013/0274688 A1 | 10/2013 | Weston |
| 2013/0310809 A1* | 11/2013 | Armstrong ............ A61M 1/0088 604/543 |
| 2013/0331822 A1 | 12/2013 | Patel et al. |
| 2013/0338613 A1 | 12/2013 | Haggstrom et al. |
| 2014/0100536 A1* | 4/2014 | Angel ............ A61M 1/0041 604/304 |
| 2014/0114268 A1 | 4/2014 | Auguste et al. |
| 2014/0166198 A1* | 6/2014 | Eckstein ............ A61M 1/0088 156/245 |
| 2014/0228791 A1 | 8/2014 | Hartwell |
| 2014/0249493 A1 | 9/2014 | Hartwell |
| 2014/0257210 A1* | 9/2014 | Leiboff ............ A61F 13/00021 604/319 |
| 2014/0316359 A1 | 10/2014 | Collinson et al. |
| 2014/0343519 A1 | 11/2014 | Weston |
| 2014/0343520 A1 | 11/2014 | Bennett et al. |
| 2014/0350494 A1* | 11/2014 | Hartwell ............ A61F 13/0216 604/319 |
| 2015/0032035 A1 | 1/2015 | Banwell et al. |
| 2015/0065966 A1 | 3/2015 | Adie et al. |
| 2015/0073358 A1 | 3/2015 | Jaeb et al. |
| 2015/0080787 A1 | 3/2015 | Blott et al. |
| 2015/0119833 A1* | 4/2015 | Coulthard ............ A61M 1/0088 604/319 |
| 2015/0141941 A1 | 5/2015 | Allen et al. |
| 2015/0165101 A1 | 6/2015 | Blott et al. |
| 2015/0173954 A1 | 6/2015 | Blott et al. |
| 2015/0190286 A1 | 7/2015 | Allen et al. |
| 2015/0202353 A1* | 7/2015 | Daughtery ............ A61M 1/0001 604/319 |
| 2015/0209492 A1 | 7/2015 | Blott et al. |
| 2015/0216733 A1 | 8/2015 | Allen et al. |
| 2015/0320990 A1 | 11/2015 | Burton et al. |
| 2016/0144084 A1 | 5/2016 | Collinson et al. |

FOREIGN PATENT DOCUMENTS

| | | |
|---|---|---|
| DE | 198 44 355 | 4/2000 |
| DE | 20 2004 017 052 | 7/2005 |
| EP | 0 392 640 | 6/1995 |
| EP | 0 441 418 | 7/1995 |
| EP | 0 465 601 | 1/1997 |
| EP | 0 620 720 | 3/1998 |
| EP | 0 777 504 | 10/1998 |
| EP | 0 865 304 | 7/2001 |
| EP | 0 751 757 | 2/2002 |
| EP | 0 853 950 | 10/2002 |
| EP | 0 708 620 | 5/2003 |
| EP | 1 088 569 | 8/2003 |
| EP | 0 993 317 | 9/2003 |
| EP | 1 018 967 | 8/2004 |
| EP | 1 100 574 | 2/2005 |
| EP | 0 688 189 | 6/2005 |
| EP | 1 440 667 | 3/2006 |
| EP | 1 284 777 | 4/2006 |
| EP | 0 982 015 | 8/2006 |
| EP | 1 448 261 | 2/2007 |
| EP | 1 171 065 | 3/2007 |
| EP | 1 227 853 | 1/2008 |
| EP | 1 476 217 | 3/2008 |
| EP | 1 233 808 | 7/2008 |
| EP | 1 977 776 | 10/2008 |
| EP | 1 513 478 | 12/2009 |
| EP | 1 905 465 | 1/2010 |
| EP | 2 172 164 | 4/2010 |
| EP | 2 319 550 | 5/2011 |
| EP | 1 578 477 | 9/2011 |
| EP | 1 487 389 | 10/2011 |
| EP | 1 169 071 | 2/2012 |
| EP | 2 021 046 | 3/2012 |
| EP | 2 127 690 | 6/2012 |
| EP | 2 462 908 | 6/2012 |
| EP | 2 529 766 | 12/2012 |
| EP | 2 413 858 | 1/2013 |
| EP | 2 545 946 | 1/2013 |
| EP | 2 659 915 | 11/2013 |
| EP | 2 628 500 | 5/2014 |
| EP | 1 339 366 | 6/2014 |
| EP | 2 051 675 | 6/2014 |
| EP | 2 544 642 | 1/2015 |
| FR | 1163907 | 10/1958 |
| GB | 2307180 | 5/1997 |
| GB | 2336546 | 6/2000 |
| GB | 2344531 | 6/2000 |
| WO | WO 2003/057070 | 7/2003 |
| WO | WO 2003/086232 | 10/2003 |
| WO | WO 2005/016179 | 2/2005 |
| WO | WO 2005/025447 | 3/2005 |
| WO | WO 2005/061025 | 7/2005 |
| WO | WO 2005/123170 | 12/2005 |
| WO | WO 2006/052338 | 5/2006 |
| WO | WO 2006/052745 | 5/2006 |
| WO | WO 2006/052839 | 5/2006 |
| WO | WO 2007/006306 | 1/2007 |
| WO | WO 2007/013049 | 2/2007 |
| WO | WO 2007/013064 | 2/2007 |
| WO | WO 2007/016590 | 2/2007 |
| WO | WO 2007/019038 | 2/2007 |
| WO | WO 2007/085396 | 8/2007 |
| WO | WO 2007/092397 | 8/2007 |
| WO | WO 2007/095180 | 8/2007 |

(56) References Cited

FOREIGN PATENT DOCUMENTS

| | | |
|---|---|---|
| WO | WO 2007/106590 | 9/2007 |
| WO | WO 2007/106591 | 9/2007 |
| WO | WO 2008/008032 | 1/2008 |
| WO | WO 2008/012278 | 1/2008 |
| WO | WO 2008/027449 | 3/2008 |
| WO | WO 2008/043067 | 4/2008 |
| WO | WO 2008/100437 | 8/2008 |
| WO | WO 2008/100440 | 8/2008 |
| WO | WO 2008/100446 | 8/2008 |
| WO | WO 2008/131895 | 11/2008 |
| WO | WO 2008/135997 | 11/2008 |
| WO | WO 2008/141470 | 11/2008 |
| WO | WO 2009/002260 | 12/2008 |
| WO | WO 2009/068665 | 6/2009 |
| WO | WO 2009/086580 | 7/2009 |
| WO | WO 2009/088925 | 7/2009 |
| WO | WO 2009/111655 | 9/2009 |
| WO | WO 2009/124100 | 10/2009 |
| WO | WO 2009/137194 | 11/2009 |
| WO | WO 2009/140376 | 11/2009 |
| WO | WO 2009/145894 | 12/2009 |
| WO | WO 2009/158125 | 12/2009 |
| WO | WO 2009/158126 | 12/2009 |
| WO | WO 2009/158127 | 12/2009 |
| WO | WO 2009/158128 | 12/2009 |
| WO | WO 2009/158129 | 12/2009 |
| WO | WO 2010/014177 | 2/2010 |
| WO | WO 2010/033271 | 3/2010 |
| WO | WO 2010/033272 | 3/2010 |
| WO | WO 2010/033769 | 3/2010 |
| WO | WO 2010/051073 | 5/2010 |
| WO | WO 2010/059712 | 5/2010 |
| WO | WO 2010/059730 | 5/2010 |
| WO | WO 2010/078166 | 7/2010 |
| WO | WO 2010/142959 | 12/2010 |
| WO | WO 2010/147533 | 12/2010 |
| WO | WO 2011/049562 | 4/2011 |
| WO | WO 2011/087871 | 7/2011 |
| WO | WO 2011/100851 | 8/2011 |
| WO | WO 2011/115908 | 9/2011 |
| WO | WO 2011/135285 | 11/2011 |
| WO | WO 2011/135286 | 11/2011 |
| WO | WO 2011/135287 | 11/2011 |
| WO | WO 2011/144888 | 11/2011 |
| WO | WO 2012/07807 | 6/2012 |
| WO | WO 2012/131237 | 10/2012 |
| WO | WO 2012/140378 | 10/2012 |
| WO | WO 2012/142002 | 10/2012 |
| WO | WO 2012/143665 | 10/2012 |
| WO | WO 2012/166428 | 12/2012 |
| WO | WO 2012/174672 | 12/2012 |
| WO | WO 2013/010907 | 1/2013 |
| WO | WO 2013/013938 | 1/2013 |
| WO | WO 2013/016239 | 1/2013 |
| WO | WO 2013/019438 | 2/2013 |
| WO | WO 2013/043972 | 3/2013 |
| WO | WO 2013/083800 | 6/2013 |
| WO | WO 2013/090810 | 6/2013 |
| WO | WO 2013/110008 | 7/2013 |
| WO | WO 2013/123005 | 8/2013 |
| WO | WO 2013/134056 | 9/2013 |
| WO | WO 2013/149078 | 10/2013 |
| WO | WO 2013/136181 | 11/2013 |
| WO | WO 2013/175306 | 11/2013 |
| WO | WO 2014/008348 | 1/2014 |
| WO | WO 2014/016759 | 1/2014 |
| WO | WO 2014/020440 | 2/2014 |
| WO | WO 2014/043238 | 3/2014 |
| WO | WO 2014/066057 | 5/2014 |
| WO | WO 2014/108476 | 7/2014 |
| WO | WO 2014/113253 | 7/2014 |
| WO | WO 2014/158526 | 10/2014 |
| WO | WO 2015/022334 | 2/2015 |
| WO | WO 2015/022340 | 2/2015 |
| WO | WO 2016/184916 | 11/2016 |

OTHER PUBLICATIONS

International Search Report and Written Opinion, re PCT Application No. PCT/EP2016/061145, dated Jul. 27, 2016.

Kendall ULTEC Hydrocolloid Dressing (4"x4"), product ordering page, web page downloaded Jul. 13, 2014.

Protz, Kerstin: "Modern Wundauflagen unterstutzen Heilungsprozess", Wundversorgung: Indikation und Anwendung, Geriatrie Journal Apr. 2005, pp. 3333-3339, with translation.

Hospitheravideo, "KCI Nanova Disclaimer Version" uploaded Mar. 30, 2015 https://www.youtube.com/watch?v=uLakPGE-R-s [Screenshots retrieved Sep. 1, 2015 in 15 pages].

Smith & Nephew, "PICO Simplified Negative Pressure Wound Therapy", sales brochure in 8 pages, Jul. 2011, Australia and New Zealand.

Smith & Nephew, "Unlock patient centric solutions with PICO", sales brochure in 2 pages, May 2014, United Kingdom.

Smith & Nephew, "Supporting healthcare professionals in incision management with PICO", sales brochure in 8 pages, Aug. 2014, United Kingdom.

Advantec MFS, Inc., "Membrane Filters" (catalog), accessed Jan. 29, 2016 (publication date unknown, but believed to be copyright 2001-2011), in 17 pages. URL: http://www.advantecmfs.com/catalog/filt/membrane.pdf#page=11.

* cited by examiner

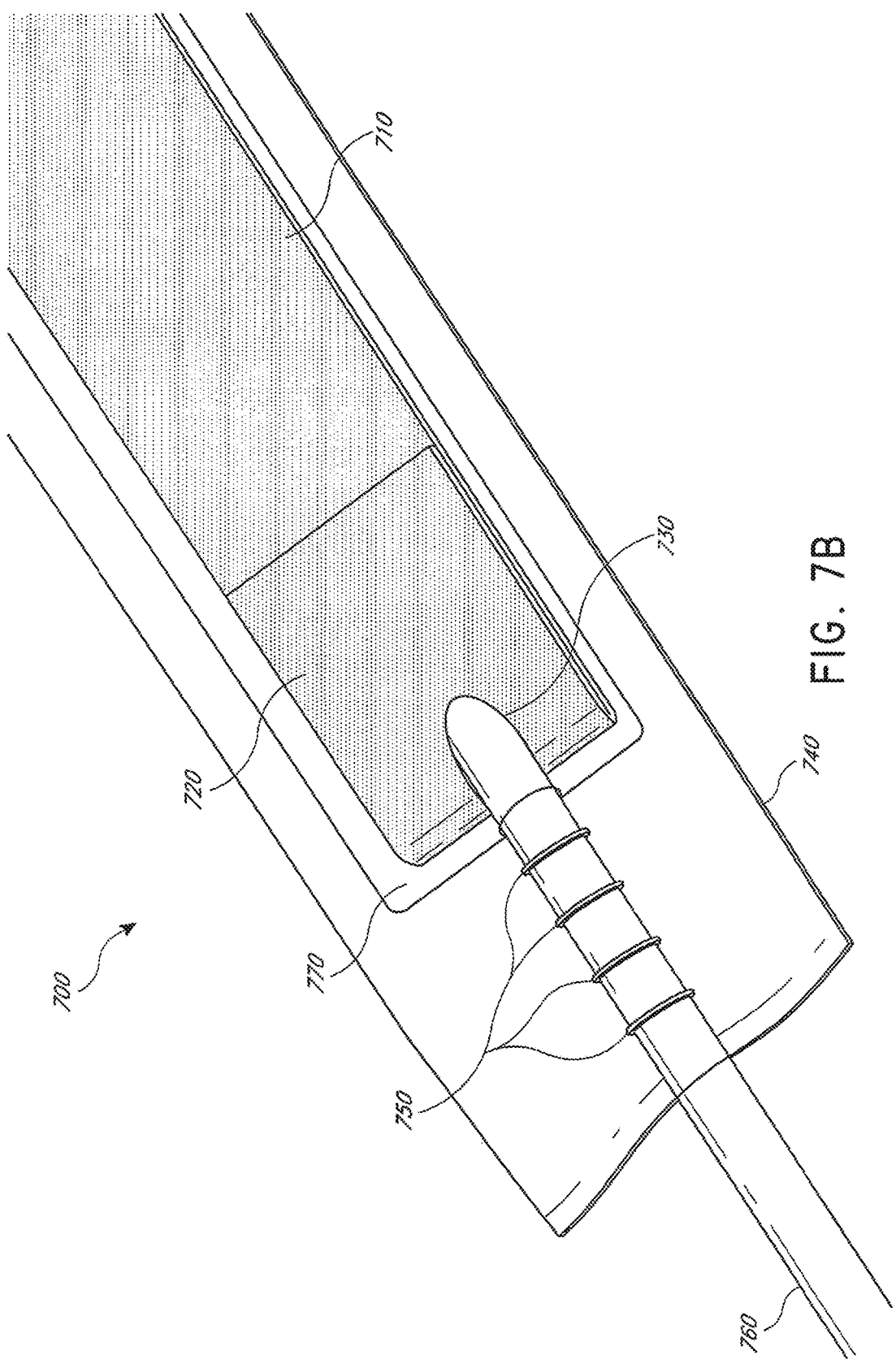

FLUIDIC CONNECTOR FOR NEGATIVE PRESSURE WOUND THERAPY

BACKGROUND OF THE INVENTION

Field of the Invention

Embodiments of the present invention relate generally to the treatment of wounds using negative pressure wound therapy and more specifically to wound treatment apparatuses including a fluidic connector for use therewith.

Description of the Related Art

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines bacteria. However, further improvements in NPWT are needed to fully realize the benefits of treatment.

Many different types of wound dressings are known for aiding in NPWT systems. These different types of wound dressings include many different types of materials and layers, for example, gauze, pads, foam pads or multi-layer wound dressings. One example of a multi-layer wound dressing is the PICO dressing, available from Smith & Nephew, which includes a superabsorbent layer beneath a backing layer to provide a canister-less system for treating a wound with NPWT. The wound dressing may be sealed to a suction port providing connection to a length of tubing, which may be used to pump fluid out of the dressing and/or to transmit negative pressure from a pump to the wound dressing.

The stiffness of certain suction ports in such close proximity to the wound site can adversely affect the healing process. Patient movement or pressure onto the wound dressing may bring the healing wound into contact with the inflexible suction port of the dressing. Such force can cause disturbance of a wound bed which can damage a wound site. This can potentially cause delays in healing of the wound site and discomfort for the patient.

It will also be appreciated that the tubing connected to the suction port is prone to obstruction. The tubing may become obstructed by movement of the patient, which may cause the tube to bend and form a kink or may place pressure onto the tubing, substantially or fully blocking the flow of fluid through the tubing. This can reduce or eliminate the negative pressure being transmitted to the wound site, and in embodiments employing a separate canister for fluid collection it can also result in accumulation of excess wound exudate at the wound site.

Further problems may arise when a suction port adhered to a top surface of a wound dressing is pulled away from the dressing. For example, if a tubing or conduit connected to the suction port is pulled in certain directions, the suction port may be peeled from the dressing. If the suction port is adhered to the dressing top surface by adhesive, such as an adhesive ring, when the suction port is compressed to the dressing top surface with the adhesive in between, this may cause localized peaks of adhesive. When a tubing or conduit is pulled to tug on the suction port, this may cause peeling of the suction port from the dressing. The localized peaks of adhesive may create areas of intense stress concentration which can lead to pin holing in the dressing after a small tug.

SUMMARY OF THE INVENTION

According to some embodiments there is provided a wound treatment apparatus comprising:

a wound dressing comprising a cover layer;

a fluidic connector configured to provide negative pressure to the wound dressing through an aperture in the cover layer, the fluidic connector comprising:

a sealing surface for sealing the fluidic connector to a top surface of the cover layer, the sealing surface comprising an opening configured to be positioned over the aperture in the cover layer; and an elongate conduit extending away from the sealing surface; and a reinforcement configured to provide additional securement between the fluidic connector and the cover layer.

In some embodiments the reinforcement is configured to be positioned between the top surface of the cover layer and the lower surface of the fluidic connector. The lower surface of the fluidic connector may be configured to be adhered to the reinforcement. The reinforcement may be positioned between the top surface of the cover layer and the lower surface of the elongate conduit. In some embodiments the reinforcement may comprise a strip of adhesive tape. The strip of adhesive tape may be configured to be positioned between the sealing surface and an edge of the cover layer. In some embodiments the reinforcement may comprise a skirt configured to be positioned between the sealing surface and the top surface of the cover layer. The skirt may comprise an opening configured to be positioned over the aperture in the cover layer. In some embodiments the sealing surface is adhered to the top surface of the cover layer with a first adhesive, and the lower surface of the fluidic connector is adhered to the reinforcement with a second adhesive. The first adhesive may be an adhesive ring that surrounds the aperture in the cover layer, and the second adhesive may be one of a second adhesive ring surrounding the first adhesive ring and an adhesive layer on a lower surface of the elongate conduit. The reinforcement may be provided over the fluidic connector. The reinforcement provided over the fluidic connector may be an adhesive tape provided over the elongate conduit and adhered to the top surface of the cover layer on opposite sides of the elongate conduit. The reinforcement may be transparent. In some embodiments the sealing surface of the fluidic connector is provided at an enlarged distal end of the fluidic connector. In some embodiments the wound treatment apparatus may further comprise a spacer layer comprising a proximal end, an elongate middle portion and a distal end; a top layer constructed from a liquid impermeable material provided over the spacer layer; and a bottom layer constructed from a liquid impermeable material provided below the spacer layer. The top layer and the bottom layer may substantially enclose the spacer layer and one or more apertures in the bottom layer beneath the distal end of the spacer layer. The spacer layer may comprise a 3D fabric material. In some embodiments the fluidic connector further comprises a filter positioned across the opening in the sealing surface. In some embodiments the wound dressing may further comprise a wound contact layer and an absorbent layer for absorbing wound exudate. The absorbent layer may be positioned between the wound contact layer and the absorbent layer. The wound dressing may further comprises one or more transmission layers between the wound contact layer and the cover layer. The one or more transmission layers may comprise 3D fabric. In some embodiments the wound treatment apparatus may comprise a transmission layer beneath the absorbent layer.

According to some embodiments there is provided a wound treatment apparatus comprising:
   a wound dressing comprising:
      a cover layer comprising an aperture;
      a wound contact layer; and
      an absorbent layer between the cover layer and the wound contact layer;
   a reinforcement layer adhered to a top surface of the cover layer, wherein the reinforcement layer comprises an opening positioned above the aperture in the cover layer;
   a fluidic connector configured to provide negative pressure to the wound dressing through the aperture in the cover layer, the fluidic connector comprising:
      a sealing surface adhered to the reinforcement layer, wherein the sealing surface surrounds the opening in the reinforcement layer;
      an upper surface positioned above the sealing surface that defines a vertical height between the sealing surface and the upper surface; and
      an elongate conduit extending laterally away from the aperture in the cover layer and the opening in the reinforcement layer, the elongate conduit extending generally parallel to the top surface of the cover layer; and
   a filter positioned beneath the upper surface of the fluidic connector to retain wound exudate within the absorbent layer during application of negative pressure to the wound dressing, wherein the filter is sized span the aperture in the cover layer.

In some embodiments the filter may be positioned between the sealing surface and the upper surface. The filter may be positioned between the upper surface and the cover layer. The filter may be positioned between the reinforcement layer and the cover layer. The filter may be positioned between the reinforcement layer and the cover layer. The sealing surface may be provided on a lower layer of the fluidic connector. The lower layer may comprise an opening that is positioned over the opening in the reinforcement layer, and the upper surface may be provided on an upper layer of the fluidic connector. The upper and lower layers may be adhered together. A spacer layer may be positioned between the upper and lower layers. In some embodiments the elongate conduit may comprise elongated portions of the upper layer, the spacer layer and the lower layer. The filter may be located between the spacer layer and the lower layer. The reinforcement layer may have an outer perimeter larger than an outer perimeter of the sealing surface. The reinforcement layer may comprise a generally circular ring. In some embodiments a first adhesive ring surrounding the opening in the reinforcement layer and surrounding the aperture in the cover layer may adhere the reinforcement layer to the cover layer, and a second adhesive ring surrounding the opening in the reinforcement layer may adhere the sealing surface to the reinforcement layer. The first adhesive ring may have a larger diameter than the second adhesive ring. The adhesive may adhere the sealing surface of the fluidic connector to both the reinforcement and to the top surface of the cover layer.

According to some embodiments there is provided an apparatus for providing negative pressure to a wound, the apparatus comprising:
   a fluidic connector configured to provide negative pressure to a wound dressing through an aperture in the wound dressing, the fluidic connector comprising:
      a sealing surface;
      an upper surface positioned above the sealing surface that defines a vertical height between the sealing surface and the upper surface; and
      an elongate conduit extending away from sealing surface;
   a reinforcement layer configured to be adhered to a top surface of the wound dressing, wherein the reinforcement layer comprises an opening configured to be positioned above the aperture in the cover layer, and
   a filter positioned beneath the upper surface of the fluidic connector and being sized to substantially span the opening in the reinforcement layer;
   wherein the sealing surface is configured to be adhered to the reinforcement layer and surround the opening in the reinforcement layer.

BRIEF DESCRIPTION OF THE DRAWINGS

FIG. 7B illustrates a close up view of an embodiment of the proximal end of the flexible fluidic connector of FIG. 7A;

DETAILED DESCRIPTION OF THE PREFERRED EMBODIMENTS

Preferred embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that may be treated using negative pressure. Wounds include, but are not limited to, open wounds, incisions, lacerations, abrasions, contusions, burns, diabetic ulcers, pressure ulcers, stoma, surgical wounds, trauma and venous ulcers or the like. Treatment of such wounds can be performed using negative pressure wound therapy, wherein a reduced or negative pressure can be applied to the wound to facilitate and promote healing of the wound. It will also be appreciated that the fluidic connector and methods as disclosed herein may be applied to other parts of the body, and are not necessarily limited to treatment of wounds.

Certain embodiments of this application related to a wound treatment apparatus employing a wound dressing and a fluidic connector, and to methods of using the same. Certain embodiments of this application relate to a fluidic connector and methods of using the same.

Figure 1A:
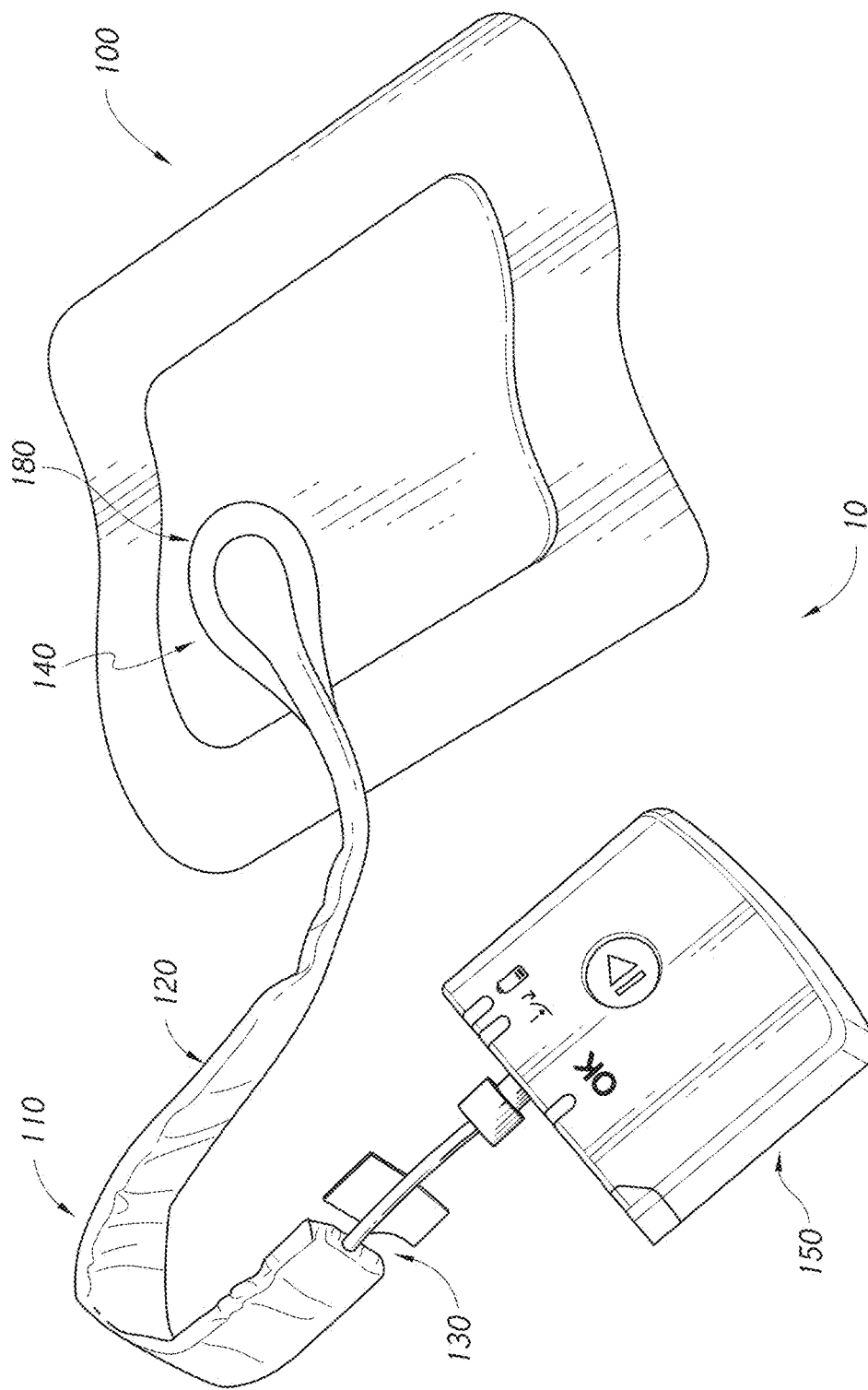
FIG. 1A illustrates an embodiment of a negative pressure wound treatment system employing a flexible fluidic connector and a wound dressing capable of absorbing and storing wound exudate.
Figure 1B:
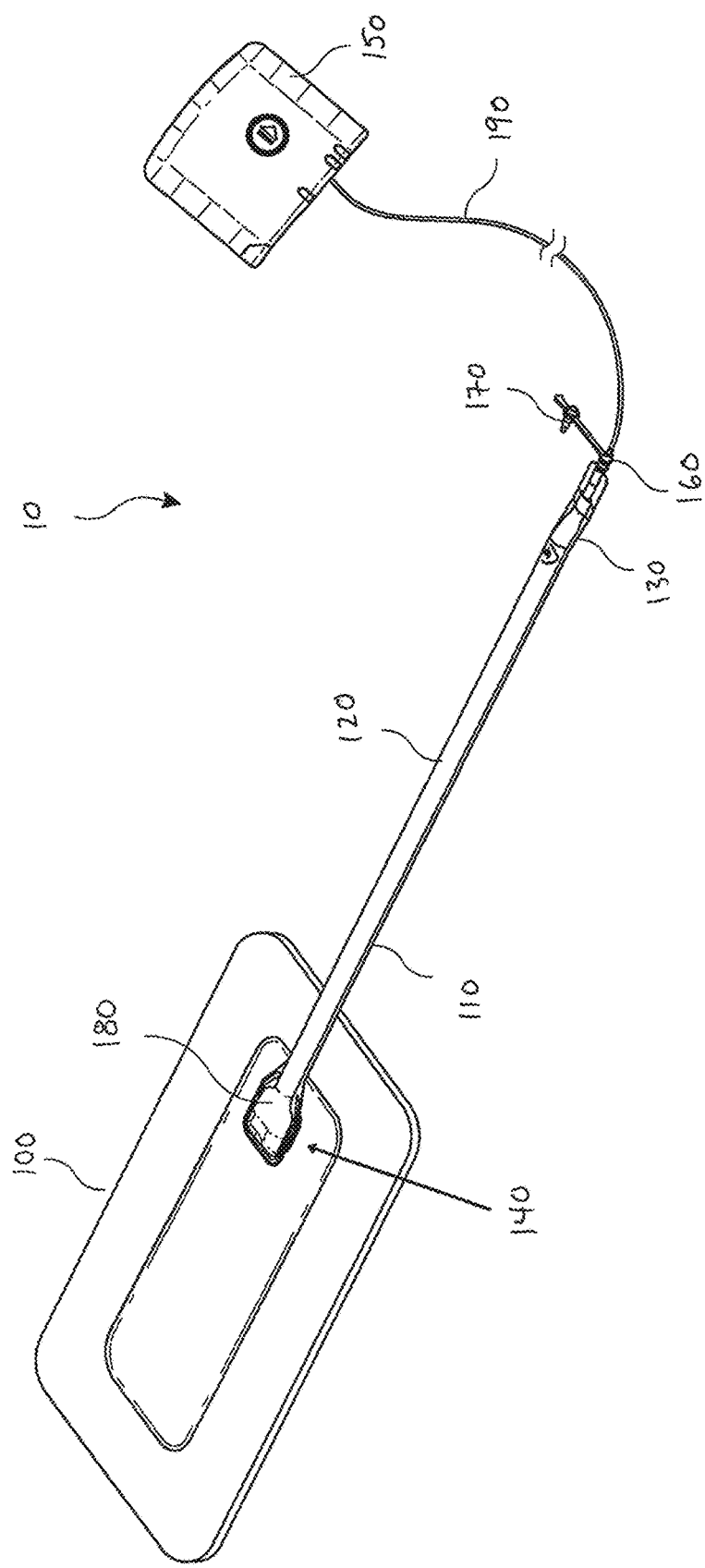
FIG. 1B illustrates an embodiment of a negative pressure wound treatment system employing a flexible fluidic connector and a wound dressing capable of absorbing and storing wound exudate.

FIGS. 1A-B illustrate embodiments of a negative pressure wound treatment system 10 employing a wound dressing 100 in conjunction with a fluidic connector 110. Here, the fluidic connector 110 may comprise an elongate conduit, more preferably a bridge 120 having a proximal end 130 and a distal end 140, and an applicator 180 at the distal end 140 of the bridge 120. An optional coupling 160 is preferably disposed at the proximal end 130 of the bridge 120. A cap 170 may be provided with the system (and can in some cases, as illustrated, be attached to the coupling 160). The cap 170 can be useful in preventing fluids from leaking out of the proximal end 130. The system 10 may include a source of negative pressure such as a pump or negative pressure unit 150 capable of supplying negative pressure. The pump may comprise a canister or other container for the storage of wound exudates and other fluids that may be removed from the wound. A canister or container may also be provided separate from the pump. In some embodiments, such as illustrated in FIGS. 1A-1B, the pump 150 can be a canisterless pump such as the PICO™ pump, as sold by Smith & Nephew. The pump 150 may be connected to the coupling 160 via a tube 190, or the pump 150 may be connected directly to the coupling 160 or directly to the bridge 120. In use, the dressing 100 is placed over a suitably-prepared wound, which may in some cases be filled with a wound packing material such as foam or gauze. The applicator 180 of the fluidic connector 110 has a sealing surface that is placed over an aperture in the dressing 100 and is sealed to the top surface of the dressing 100. Either before, during, or after connection of the fluidic connector 110 to the dressing 100, the pump 150 is connected via the tube 190 to the coupling 160, or is connected directly to the coupling 160 or to the bridge 120. The pump is then activated, thereby supplying negative pressure to the wound. Application of negative pressure may be applied until a desired level of healing of the wound is achieved.

Figure 2A:
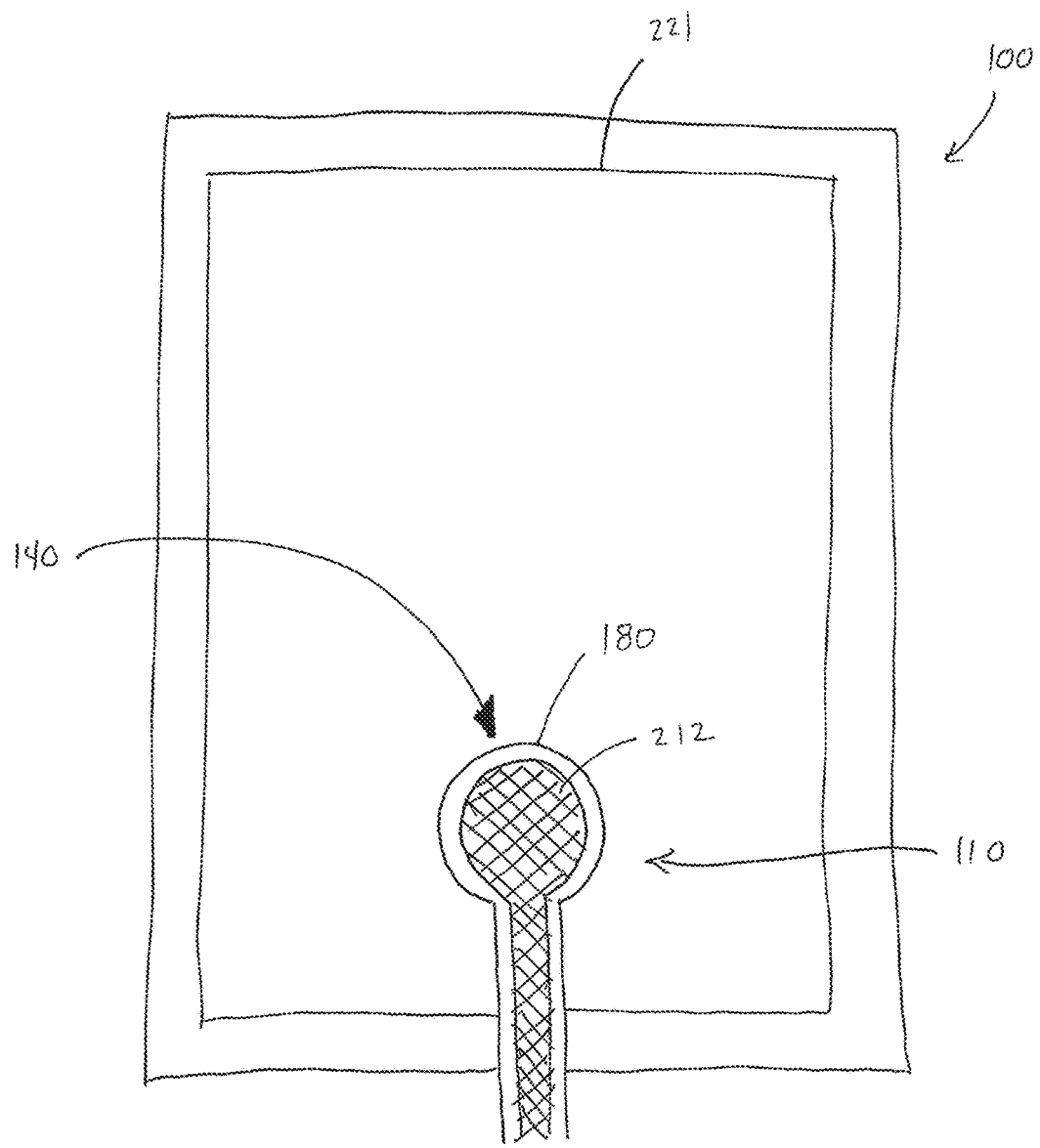
FIG. 2A illustrates an embodiment of a negative pressure wound treatment system employing a flexible fluidic connector and a wound dressing capable of absorbing and storing wound exudate.
Figure 2B:
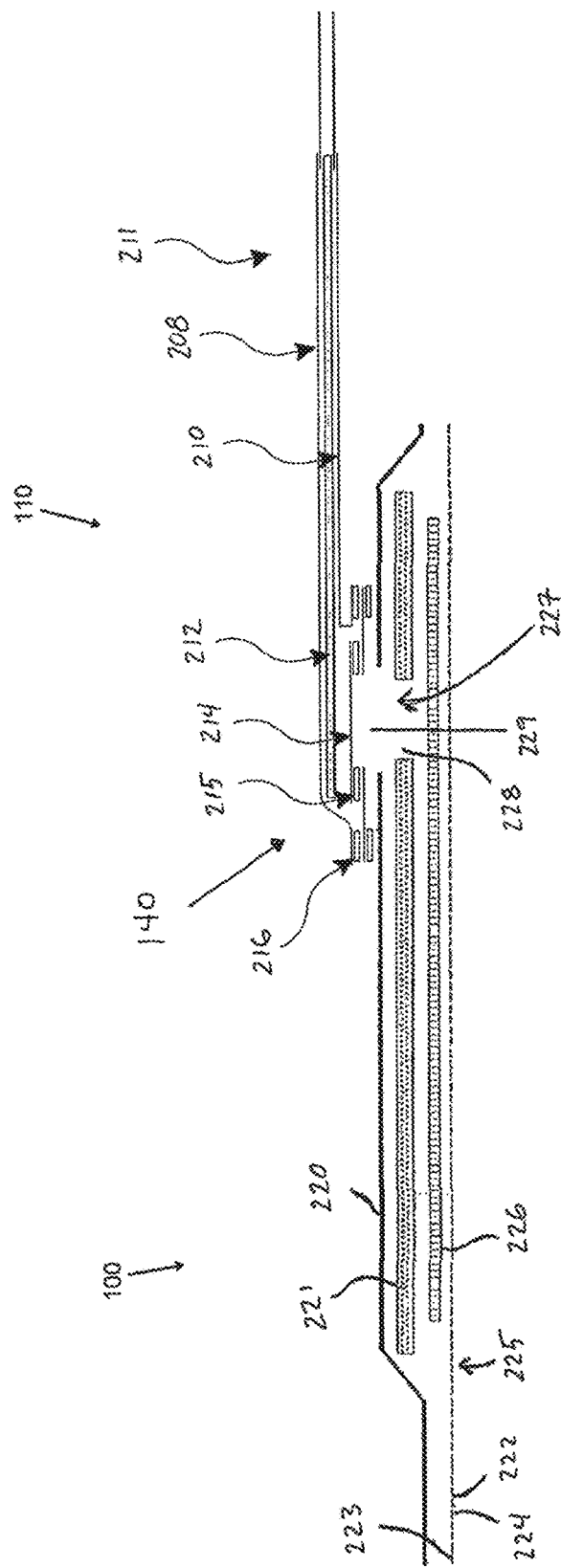
FIG. 2B illustrates a cross section of an embodiment of a fluidic connector connected to a wound dressing.

With reference initially to FIGS. 2A-B, treatment of a wound with negative pressure in certain embodiments of the application uses a wound dressing 100 capable of absorbing and storing wound exudate in conjunction with a flexible fluidic connector 110. In some embodiments, the wound dressing 100 may be substantially similar to wound dressings and have the same or similar components as those described throughout International Patent Publication WO2013175306, WO2014020440, WO2014020443 and U.S. Publication No. 2011/0282309 A1, which are incorporated by reference in their entireties. In other embodiments (not shown), the wound dressing may simply comprise one or more backing layers configured to form a sealed chamber over the wound site. In some embodiments, it may be preferable for the wound site to be filled partially or completely with a wound packing material. This wound packing material is optional, but may be desirable in certain wounds, for example deeper wounds. The wound packing material can be used in addition to the wound dressing 100. The wound packing material generally may comprise a porous and conformable material, for example foam (including reticulated foams), and gauze. Preferably, the wound packing material is sized or shaped to fit within the wound site so as to fill any empty spaces. The wound dressing 100 may then be placed over the wound site and wound packing material overlying the wound site. When a wound packing material is used, once the wound dressing 100 is sealed over the wound site, negative pressure may be transmitted from a pump or other source of negative pressure through a flexible tubing via the fluidic connector 110 to the wound dressing 100, through the wound packing material, and finally to the wound site. This negative pressure draws wound exudate and other fluids or secretions away from the wound site.

As shown in FIG. 2A, the fluidic connector 110 preferably comprises an enlarged distal end, or head 140 that is in fluidic communication with the dressing 100 as will be described in further detail below. In one embodiment, the enlarged distal end has a round or circular shape. The head 140 is illustrated here as being positioned near an edge of the dressing 100, but may also be positioned at any location on the dressing. For example, some embodiments may provide for a centrally or off-centered location not on or near an edge or corner of the dressing 100. In some embodiments, the dressing 10 may comprise two or more fluidic connectors 110, each comprising one or more heads 140, in fluidic communication therewith. In a preferred embodiment, the head 140 may measure 30 mm along its widest edge. The head 140 forms at least in part the applicator 180, described above, that is configured to seal against a top surface of the wound dressing.

FIG. 2B illustrates a cross-section through a wound dressing 100 similar to the wound dressing 10 as shown in FIG. 1B and described in International Patent Publication WO2013175306, which is incorporated by reference in its entirety, along with fluidic connector 110. The wound dressing 100, which can alternatively be any wound dressing embodiment disclosed herein or any combination of features of any number of wound dressing embodiments disclosed herein, can be located over a wound site to be treated. The dressing 100 may be placed to as to form a sealed cavity over the wound site. In a preferred embodiment, the dressing 100 comprises a top or cover layer, or backing layer 220 attached to an optional wound contact layer 222, both of which are described in greater detail below. These two layers 220, 222 are preferably joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As illustrated in FIG. 2B, the wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 and an upper surface 223. The perforations 225 preferably comprise through holes in the wound contact layer 222 which enable fluid to flow through the layer 222. The wound contact layer 222 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 222 may help maintain the integrity of the entire dressing 100 while also creating an air tight seal around the absorbent pad in order to maintain negative pressure at the wound.

Some embodiments of the wound contact layer 222 may also act as a carrier for an optional lower and upper adhesive layer (not shown). For example, a lower pressure sensitive adhesive may be provided on the lower surface 224 of the wound dressing 100 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 226 of porous material can be located above the wound contact layer 222. This porous layer, or transmission layer, 226 allows transmission of fluid including liquid and gas away from a wound site into upper layers of the wound dressing. In particular, the transmission layer 226 preferably ensures that an open air channel can be maintained to communicate negative pressure over the wound area even when the absorbent layer has absorbed substantial amounts of exudates. The layer 226 should preferably remain open under the typical pressures that will be applied during negative pressure wound therapy as described above, so that the whole wound site sees an equalized negative pressure. The layer 226 may be formed of a material having a three dimensional structure. For example, a knitted or woven spacer fabric (for example Baltex 7970 weft knitted polyester) or a non-woven fabric could be used.

In some embodiments, the transmission layer 226 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 221 helps lock the liquid away or itself wicks the liquid onwards towards the cover layer where it can be transpired.

Preferably, to improve the liquid flow across the transmission layer 226 (that is to say perpendicular to the channel region formed between the top and bottom spacer layers, the 3D fabric may be treated with a dry cleaning agent (such as, but not limited to, Perchloro Ethylene) to help remove any manufacturing products such as mineral oils, fats and/or waxes used previously which might interfere with the hydrophilic capabilities of the transmission layer. In some embodiments, an additional manufacturing step can subsequently be carried out in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 221 of absorbent material is provided above the transmission layer 226. The absorbent material, which comprise a foam or non-woven natural or synthetic material, and which may optionally comprise a super-absorbent material, forms a reservoir for fluid, particularly liquid, removed from the wound site. In some embodiments, the layer 10 may also aid in drawing fluids towards the backing layer 220.

The material of the absorbent layer 221 may also prevent liquid collected in the wound dressing 100 from flowing freely within the dressing, and preferably acts so as to contain any liquid collected within the dressing. The absorbent layer 221 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 and/or Chem-Posite™ 11C-450. In some embodiments, the absorbent layer 221 may comprise a composite comprising super-absorbent powder, fibrous material such as cellulose, and bonding fibers. In a preferred embodiment, the composite is an airlaid, thermally-bonded composite.

In some embodiments, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 227 is preferably provided in the backing layer 220 to allow a negative pressure to be applied to the dressing 100. The fluidic connector 110 is preferably attached or sealed to the top of the backing layer 220 over the orifice 227 made into the dressing 100, and communicates negative pressure through the orifice 227. A length of tubing may be coupled at a first end to the fluidic connector 110 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 110 may be adhered and sealed to the backing layer 220 using an adhesive such as an acrylic, cyanoacrylate, epoxy, UV curable or hot melt adhesive. The fluidic connector 110 may be formed from a soft polymer, for example a polyethylene, a polyvinyl chloride, a silicone or polyurethane having a hardness of 30 to 90 on the Shore A scale. In some embodiments, the fluidic connector 110 may be made from a soft or conformable material.

Preferably the absorbent layer 221 includes at least one through hole 228 located so as to underlie the fluidic connector 110. The through hole 228 may in some embodiments be the same size as the opening 227 in the backing layer, or may be bigger or smaller. As illustrated in FIG. 2B a single through hole can be used to produce an opening underlying the fluidic connector 110. It will be appreciated that multiple openings could alternatively be utilized. Additionally should more than one port be utilized according to certain embodiments of the present disclosure one or multiple openings may be made in the absorbent layer and the obscuring layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 228 is preferably provided in the absorbent layer 221 beneath the orifice 227 such that the orifice is connected directly to the transmission layer 226. This allows the negative pressure applied to the fluidic connector 110 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided. In further alternative embodiments, additional layers such as another transmission layer or an obscuring layer such as described in International Patent Publication WO2014020440 may be provided over the absorbent layer 221 and beneath the backing layer 220.

The backing layer 220 is preferably gas impermeable, but moisture vapor permeable, and can extend across the width of the wound dressing 100. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 220 and a wound site where a negative pressure can be established. The backing layer 220 is preferably sealed to the wound contact layer 222 in a border region around the circumference of the dressing, ensuring that no air is drawn in through the border area, for example via adhesive or welding techniques. The backing layer 220 protects the wound from external bacterial contamination (bacterial barrier) and allows liquid from wound exudates to be transferred through the layer and evaporated from the film outer surface. The backing layer 220 preferably comprises two layers; a polyurethane film and an adhesive pattern spread onto the film. The polyurethane film is preferably moisture vapor permeable and may be manufactured from a material that has an increased water transmission rate when wet. In some embodiments the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which may otherwise seep through the seal around the perimeter of the dressing leading to the formation of leaks. As illustrated in FIGS. 2A-2B, the absorbent layer 221 may define a smaller perimeter than that of the backing layer 220, such that a boundary or border region is defined between the edge of the absorbent layer 221 and the edge of the backing layer 220.

As shown in FIG. 2B, one embodiment of the wound dressing 100 comprises an aperture 228 in the absorbent layer 221 situated underneath the fluidic connector 110. In use, for example when negative pressure is applied to the dressing 100, a wound facing portion of the fluidic connector may thus come into contact with the transmission layer 226, which can thus aid in transmitting negative pressure to the wound site even when the absorbent layer 221 is filled with wound fluids. Some embodiments may have the backing layer 220 be at least partly adhered to the transmission layer 226. In some embodiments, the aperture 228 is at least 1-2 mm larger than the diameter of the wound facing portion of the fluidic connector 11, or the orifice 227.

In particular for embodiments with a single fluidic connector 110 and through hole, it may be preferable for the fluidic connector 110 and through hole to be located in an off-center position as illustrated in FIG. 2A. Such a location may permit the dressing 100 to be positioned onto a patient such that the fluidic connector 110 is raised in relation to the remainder of the dressing 100. So positioned, the fluidic connector 110 and the filter 214 may be less likely to come into contact with wound fluids that could prematurely occlude the filter 214 so as to impair the transmission of negative pressure to the wound site.

Turning now to the fluidic connector 110, preferred embodiments comprise a sealing surface 216, a bridge 211 (corresponding to bridge 120 in FIGS. 1A-1B) with a proximal end 130 and a distal end 140, and a filter 214. The sealing surface 216 preferably forms the applicator previously described that is sealed to the top surface of the wound dressing. In some embodiments a bottom layer of the fluidic connector 110 may comprise the sealing surface 216, such as layer 540 in FIG. 5C below. The fluidic connector 110 may further comprise an upper surface vertically spaced from the sealing surface 216, which in some embodiments is defined by a separate upper layer of the fluidic connector such as layer 510 in FIG. 5C below. In other embodiments the upper surface and the lower surface may be formed from the same piece of material. In some embodiments the sealing surface 216 may comprise at least one aperture 229 therein to communicate with the wound dressing. In some embodiments the filter 214 may be positioned across the opening 229 in the sealing surface, and may span the entire opening 229. The sealing surface 216 may be configured for sealing the fluidic connector to the cover layer of the wound dressing, and may comprise an adhesive or weld. In some embodiments, the sealing surface 216 may be placed over an orifice in the cover layer with optional spacer elements 215 configured to create a gap between the filter 214 and the transmission layer 226. In other embodiments, the sealing surface 216 may be positioned over an orifice in the cover layer and an aperture in the absorbent layer 220, permitting the fluidic connector 110 to provide air flow through the transmission layer 226. In some embodiments, the bridge 211 may comprise a first fluid passage 212 in communication with a source of negative pressure, the first fluid passage 212 comprising a porous material, such as a 3D knitted material, which may be the same or different than the porous layer 226 described previously. The bridge 211 is preferably encapsulated by at least one flexible film layer 208, 210 having a proximal and distal end and configured to surround the first fluid passage 212, the distal end of the flexible film being connected the sealing surface 216. The filter 214 is configured to substantially prevent wound exudate from entering the bridge, and spacer elements 215 are configured to prevent the fluidic connector from contacting the transmission layer 226. These elements will be described in greater detail below.

Figure 7A:
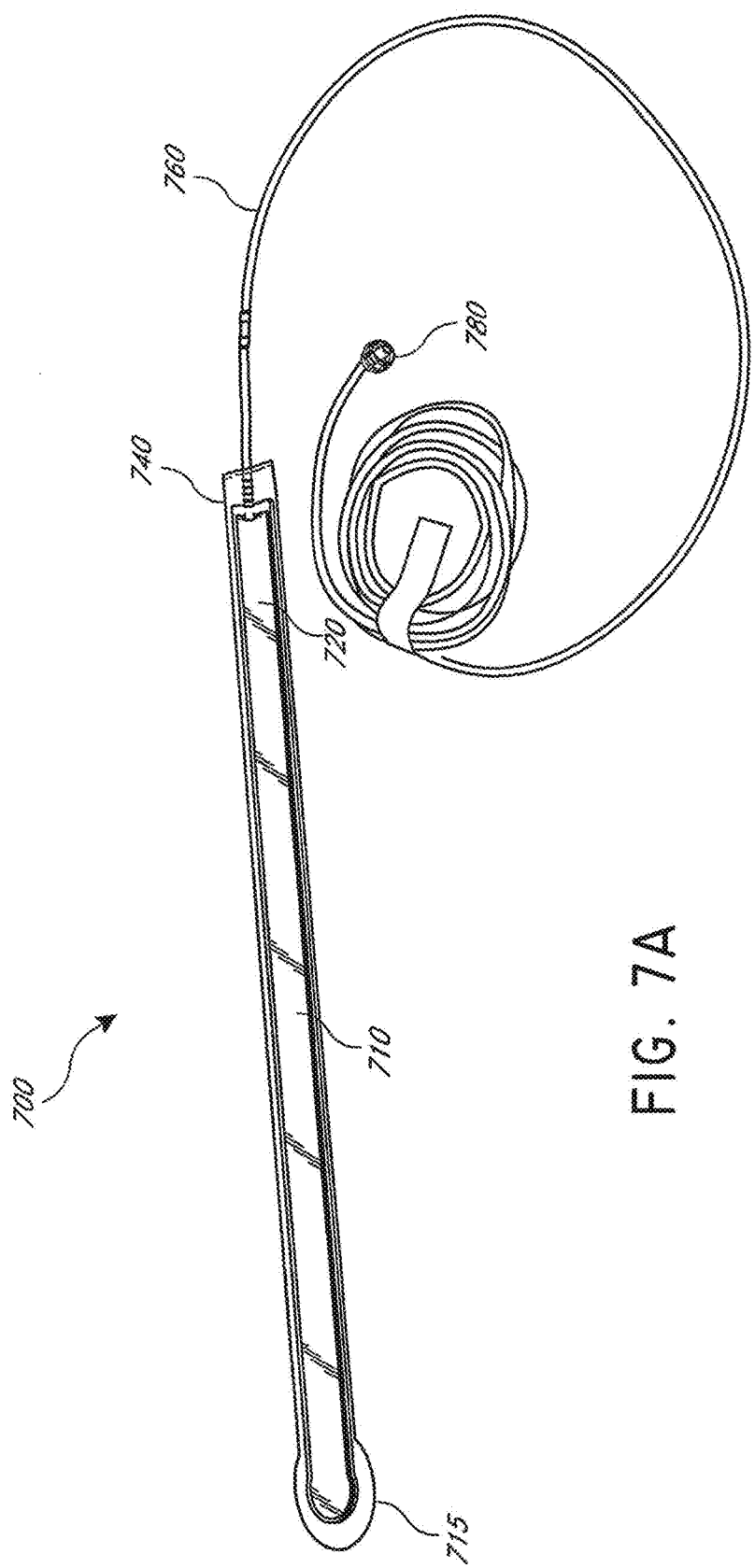
FIG. 7A illustrates a perspective view of an embodiment of a flexible fluidic connector.
Figure 7C:
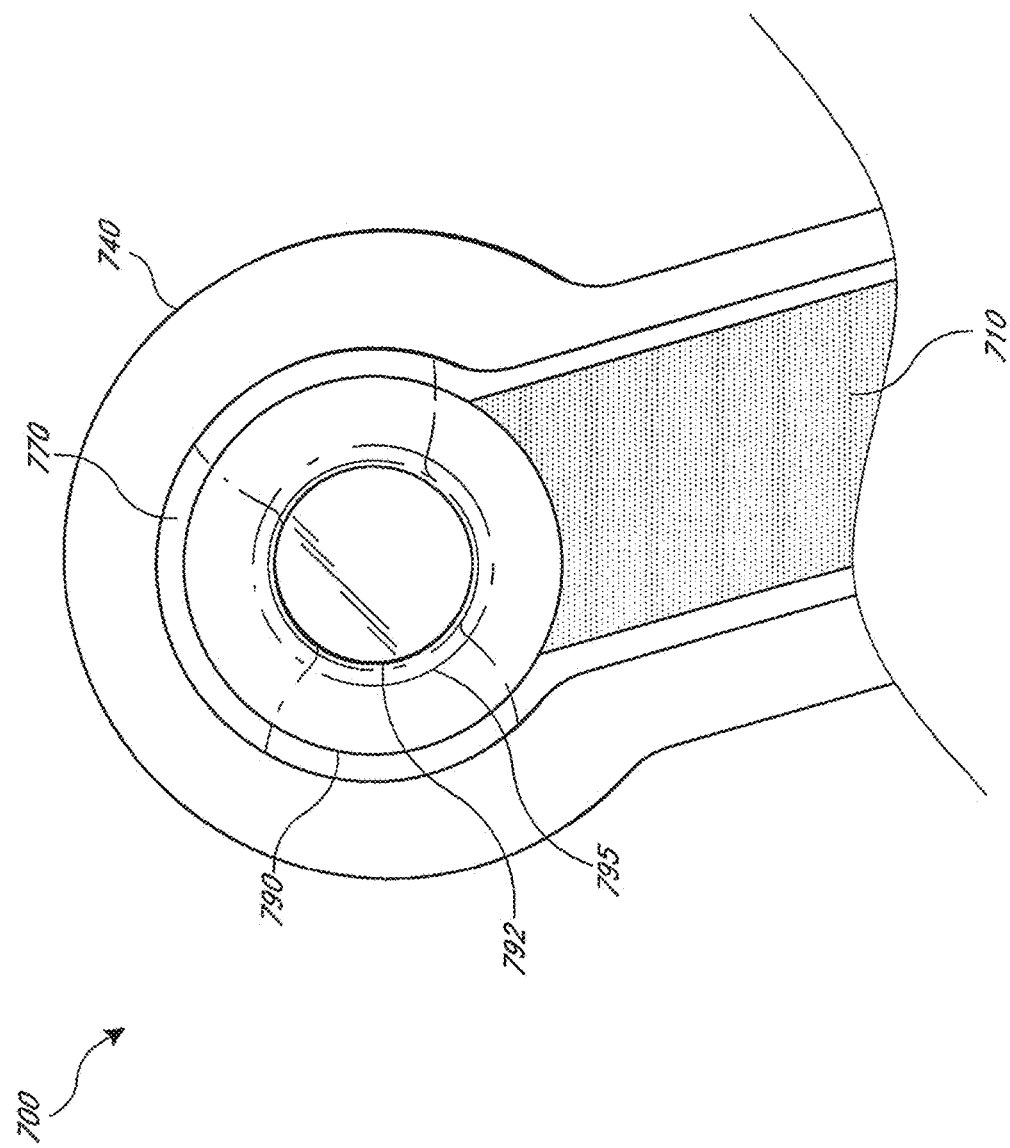
FIG. 7C illustrates a close up view of the bottom of the distal end of the flexible fluidic connector of FIG. 7A.

Some embodiments may further comprise an optional second fluid passage positioned above the first fluid passage 212. For example, some embodiments may provide for an air leak may be disposed at the proximal end of the top layer that is configured to provide an air path into the first fluid passage 212 and dressing 100 similar to the suction adapter 701 as shown in FIGS. 7A-C and described in U.S. Pat. No. 8,801,685, which is incorporated by reference herein in its entirety.

Preferably, the fluid passage 212 is constructed from a compliant material that is flexible and that also permits fluid to pass through it if the spacer is kinked or folded over. Suitable materials for the fluid passage 212 include without limitation foams, including open-cell foams such as polyethylene or polyurethane foam, meshes, 3D knitted fabrics, non-woven materials, and fluid channels. In some embodiments, the fluid passage 212 may be constructed from materials similar to those described above in relation to the transmission layer 226. Advantageously, such materials used in the fluid passage 212 not only permit greater patient comfort, but may also provide greater kink resistance, such that the fluid passage 212 is still able to transfer fluid from the wound toward the source of negative pressure while being kinked or bent.

In some embodiments, the fluid passage 212 may be comprised of a wicking fabric, for example a knitted or woven spacer fabric (such as a knitted polyester 3D fabric, Baltex 7970®, or Gehring 879®) or a nonwoven fabric. These materials selected are preferably suited to channeling wound exudate away from the wound and for transmitting negative pressure and/or vented air to the wound site, and may also confer a degree of kinking or occlusion resistance to the fluid passage 212. In some embodiments, the wicking fabric may have a three-dimensional structure, which in some cases may aid in wicking fluid or transmitting negative pressure. In certain embodiments, including wicking fabrics, these materials remain open and capable of communicating negative pressure to a wound area under the typical pressures used in negative pressure therapy, for example between 40 to 150 mmHg. In some embodiments, the wicking fabric may comprise several layers of material stacked or layered over each other, which may in some cases be useful in preventing the fluid passage 212 from collapsing under the application of negative pressure. In other embodiments, the wicking fabric used in the fluid passage 212 may be between 1.5 mm and 6 mm; more preferably, the wicking fabric may be between 3 mm and 6 mm thick, and may be comprised of either one or several individual layers of wicking fabric. In other embodiments, the fluid passage 212 may be between 1.2-3 mm thick, and preferably thicker than 1.5 mm. Some embodiments, for example a suction adapter used with a dressing which retains liquid such as wound exudate, may employ hydrophobic layers in the fluid passage 212, and only gases may travel through the fluid passage 212. Additionally, and as described previously, the materials used in the system are preferably conformable and soft, which may help to avoid pressure ulcers and other complications which may result from a wound treatment system being pressed against the skin of a patient.

Preferably, the filter element 214 is impermeable to liquids, but permeable to gases, and is provided to act as a liquid barrier and to ensure that no liquids are able to escape from the wound dressing 100. The filter element 214 may also function as a bacterial barrier. Typically the pore size is 0.2 µm. Suitable materials for the filter material of the filter element 214 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the cover film over the orifice. For example, the filter element 214 may be molded into the fluidic connector 110, or may be adhered to one or both of the top of the cover layer and bottom of the suction adapter 110 using an adhesive such as, but not limited to, a UV cured adhesive.

It will be understood that other types of material could be used for the filter element 214. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments of the invention, filter element 214 comprises a support layer and an acrylic co-polymer membrane formed on the support layer. Preferably the wound dressing 100 according to certain embodiments of the present invention uses microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 214 may also include an odor absorbent material, for example activated charcoal, carbon fiber cloth or Vitec Carbotec-RT Q2003073 foam, or the like. For example, an odor absorbent material may form a layer of the filter element 214 or may be sandwiched between microporous hydrophobic membranes within the filter element. The filter element 214 thus enables gas to be exhausted through the orifice. Liquid, particulates and pathogens however are contained in the dressing.

The wound dressing 100 may comprise spacer elements 215 in conjunction with the fluidic connector 110 and the filter 214. With the addition of such spacer elements 215 the fluidic connector 110 and filter 214 may be supported out of direct contact with the absorbent layer 220 and/or the transmission layer 226. The absorbent layer 220 may also act as an additional spacer element to keep the filter 214 from contacting the transmission layer 226. Accordingly, with such a configuration contact of the filter 214 with the transmission layer 226 and wound fluids during use may thus be minimized.

In particular for embodiments with a single fluidic connector 110 and through hole, it may be preferable for the fluidic connector 110 and through hole to be located in an off-center position as illustrated in FIGS. 2A-B. Such a location may permit the dressing 100 to be positioned onto a patient such that the fluidic connector 110 is raised in relation to the remainder of the dressing 100. So positioned, the fluidic connector 110 and the filter 214 may be less likely to come into contact with wound fluids that could prematurely occlude the filter 214 so as to impair the transmission of negative pressure to the wound site.

Figure 3A:
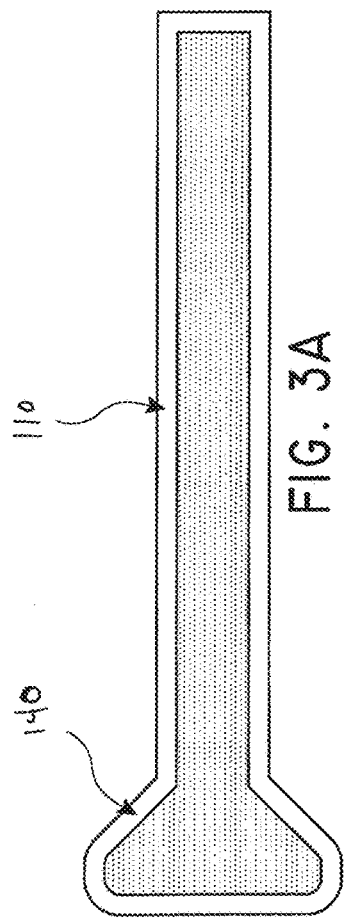
FIG. 3A-C illustrate various embodiments of the enlarged end of a flexible fluidic connector.
Figure 3B:
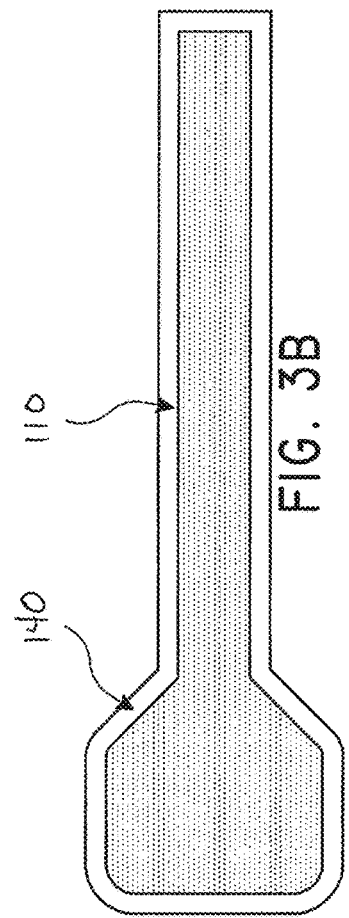
Figure 3C:
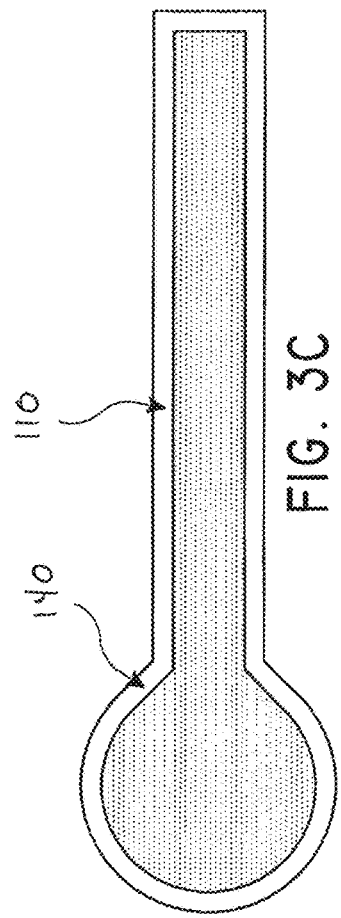

FIGS. 3A-C illustrate various embodiments of the head 140 of the fluidic connector 110. Preferably, the fluidic connector 110 illustrated in FIG. 2A is enlarged at the distal end to be placed over an orifice in the cover layer and the aperture in the absorbent layer of a wound dressing, for example wound dressing 100 of FIGS. 2A-B, and may form a "teardrop" or other enlarged shape. FIG. 3A illustrates a fluidic connector 110 with a substantially triangular head 140. FIG. 3B illustrates a fluidic connector 110 with a substantially pentagonal head 140. FIG. 3C illustrates a fluidic connector 110 with a substantially circular head 140.

Figure 4A:
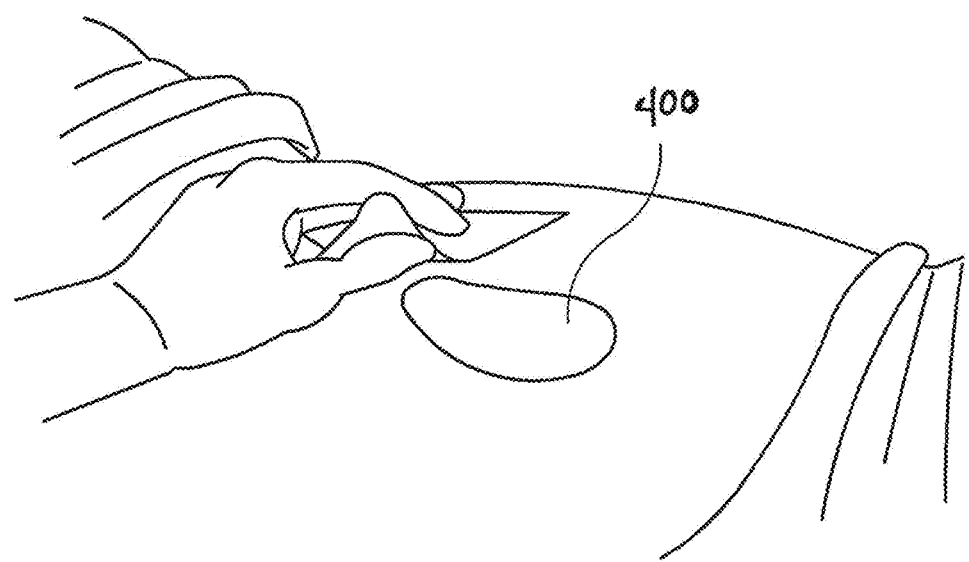
FIGS. 4A-D illustrate the use and application of an embodiment of a wound treatment system onto a patient.

FIGS. 4A-D illustrate the use of an embodiment of a negative pressure therapy wound treatment system being used to treat a wound site on a patient. FIG. 4A shows a wound site 400 being cleaned and prepared for treatment. Here, the healthy skin surrounding the wound site 400 is preferably cleaned and excess hair removed or shaved. The wound site 400 may also be irrigated with sterile saline solution if necessary. Optionally, a skin protectant may be applied to the skin surrounding the wound site 400. If necessary, a wound packing material, such as foam or gauze, may be placed in the wound site 400. This may be preferable if the wound site 400 is a deeper wound.

Figure 4B:
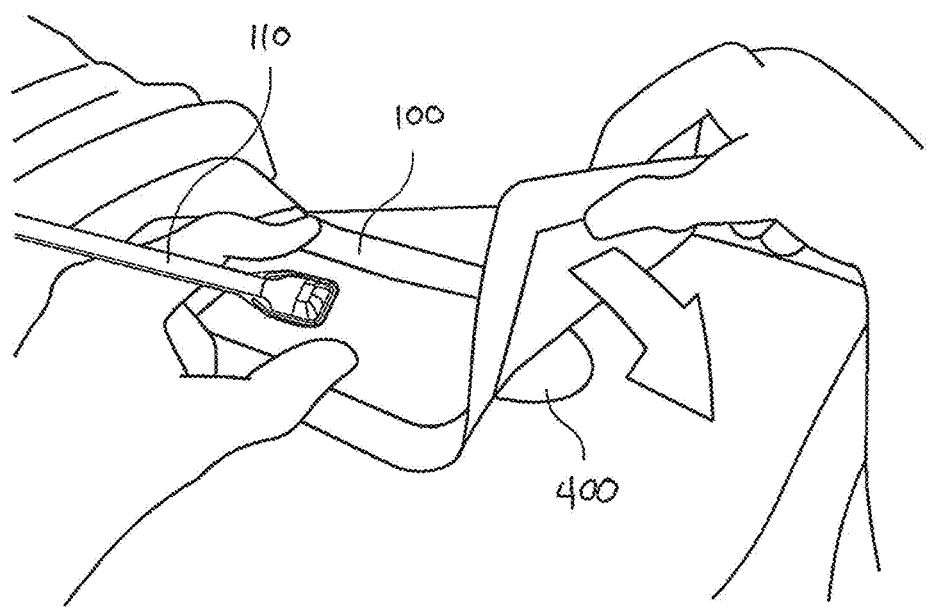

After the skin surrounding the wound site 400 is dry, and with reference now to FIG. 4B, the wound dressing 100 may be positioned and placed over the wound site 400. Preferably, the wound dressing 100 is placed with the wound contact layer over and/or in contact with the wound site 400. In some embodiments, an adhesive layer is provided on the lower surface of the wound contact layer, which may in some cases be protected by an optional release layer to be removed prior to placement of the wound dressing 100 over the wound site 400. Preferably, the dressing 100 is positioned such that the fluidic connector 110 is in a raised position with respect to the remainder of the dressing 10 so as to avoid fluid pooling around the port. In some embodiments, the dressing 100 is positioned so that the fluidic connector 110 is not directly overlying the wound, and is level with or at a higher point than the wound. To help ensure adequate sealing for TNP, the edges of the dressing 100 are preferably smoothed over to avoid creases or folds.

Figure 4C:
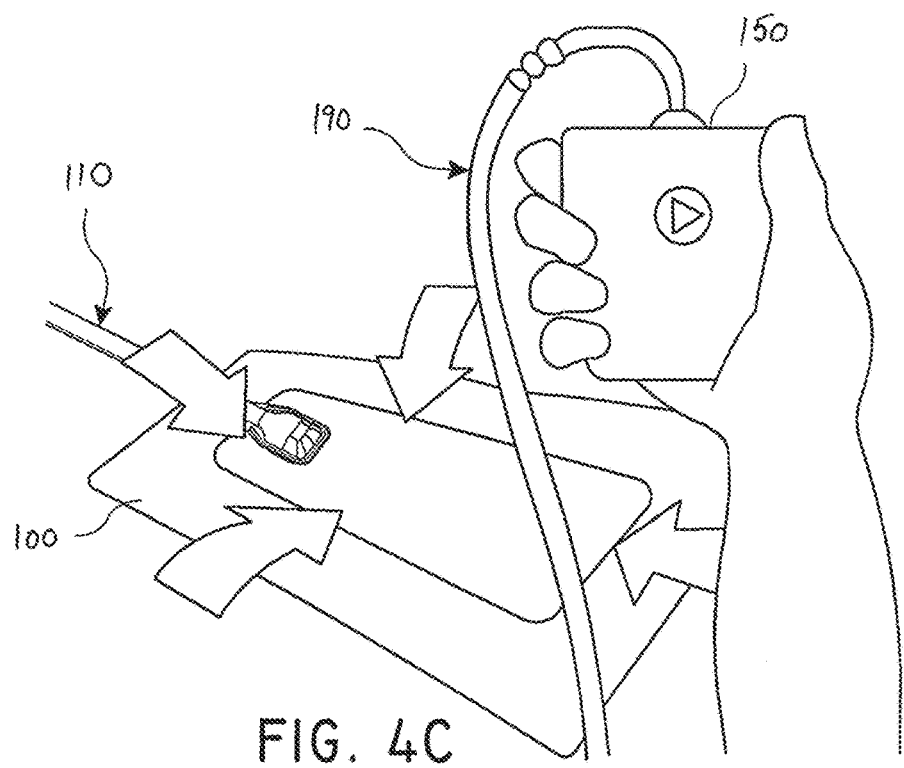

With reference now to FIG. 4C, the dressing 10 is connected to the pump 150. The pump 150 is configured to apply negative pressure to the wound site via the dressing 100, and typically through a conduit. In some embodiments, and as described herein, a fluidic connector 110 may be used to join the conduit 190 from the pump to the dressing 100. Where the fluidic connector is adhered to the top layer of the wound dressing, a length of tubing may be coupled at a first end of the fluidic connector such that the tubing, or conduit, extends away from the fluidic connector parallel to the top of the dressing. In some embodiments the conduit may comprise a fluidic connector. It is expressly contemplated that a conduit may be a soft bridge, a hard tube, or any other apparatus which may serve to transport fluid. Upon the application of negative pressure with the pump 150, the dressing 100 may in some embodiments partially collapse and present a wrinkled appearance as a result of the evacuation of some or all of the air underneath the dressing 100. In some embodiments, the pump 150 may be configured to detect if any leaks are present in the dressing 100, such as at the interface between the dressing 100 and the skin surrounding the wound site 400. Should a leak be found, such leak is preferably remedied prior to continuing treatment.

Figure 4D:
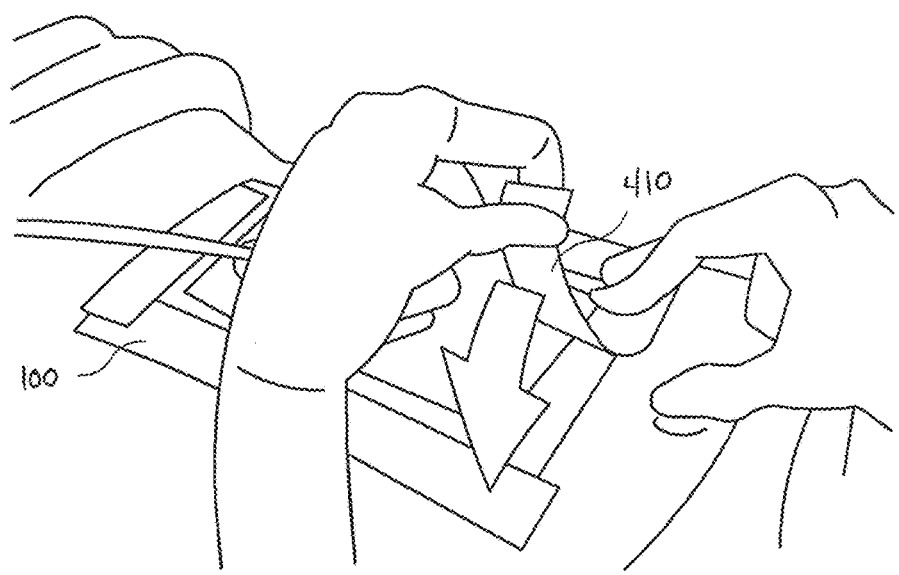

Turning to FIG. 4D, additional fixation strips 410 may also be attached around the edges of the dressing 100. Such fixation strips 410 may be advantageous in some situations so as to provide additional sealing against the skin of the patient surrounding the wound site 400. For example, the fixation strips 410 may provide additional sealing for when a patient is more mobile. In some cases, the fixation strips 410 may be used prior to activation of the pump 150, particularly if the dressing 100 is placed over a difficult to reach or contoured area.

Treatment of the wound site 400 preferably continues until the wound has reached a desired level of healing. In some embodiments, it may be desirable to replace the dressing 100 after a certain time period has elapsed, or if the dressing is full of wound fluids. During such changes, the pump 150 may be kept, with just the dressing 100 being changed.

Further details of dressings and other apparatuses that may be used with the, fluidic connectors described herein include, but are not limited to, dressings described in International Patent Publication WO 2012020440 and WO2014020443, the entireties of which are hereby incorporated by reference.

Figure 5A:
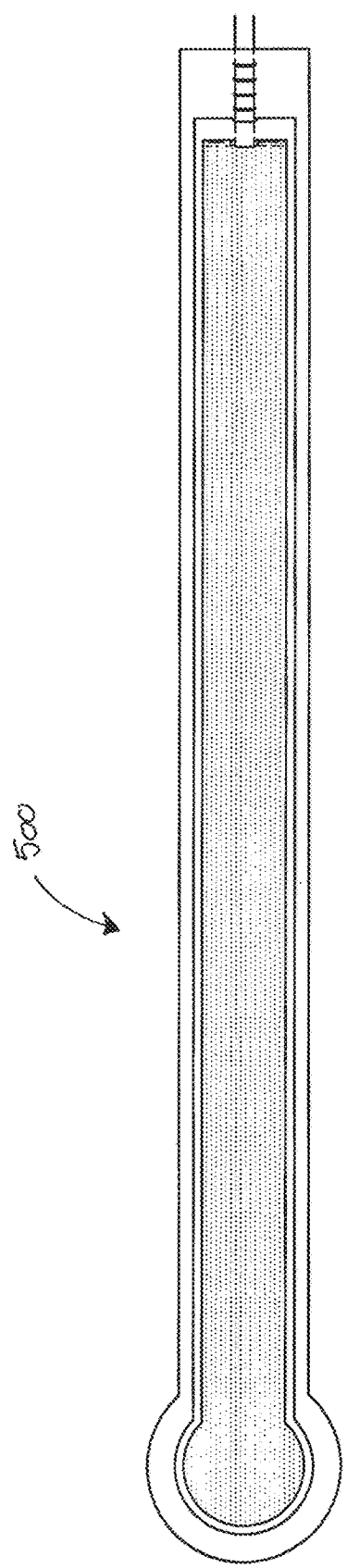
FIG. 5A illustrates a top view of an embodiment of a flexible fluidic connector.
Figure 5B:
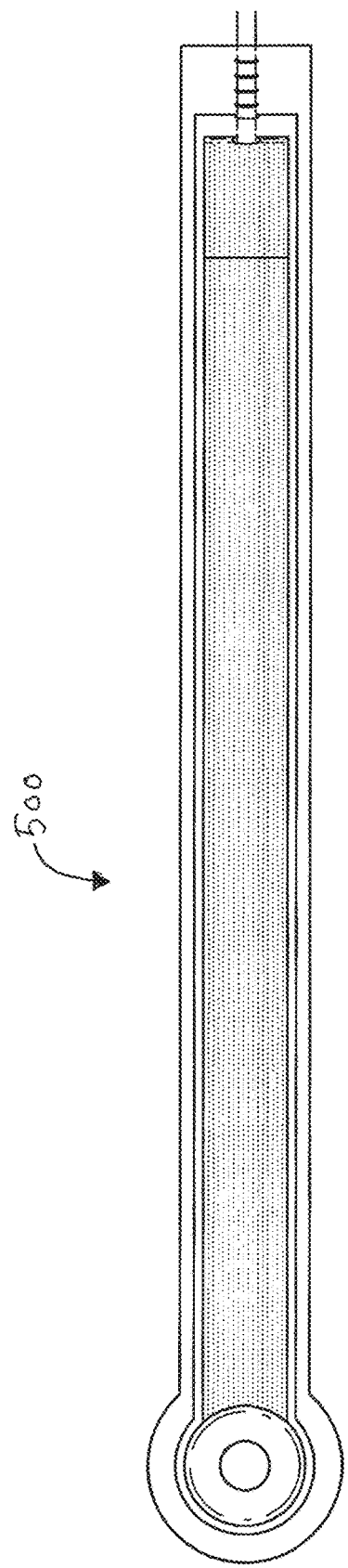
FIG. 5B illustrates a bottom view of an embodiment of a flexible fluidic connector.
Figure 5C:
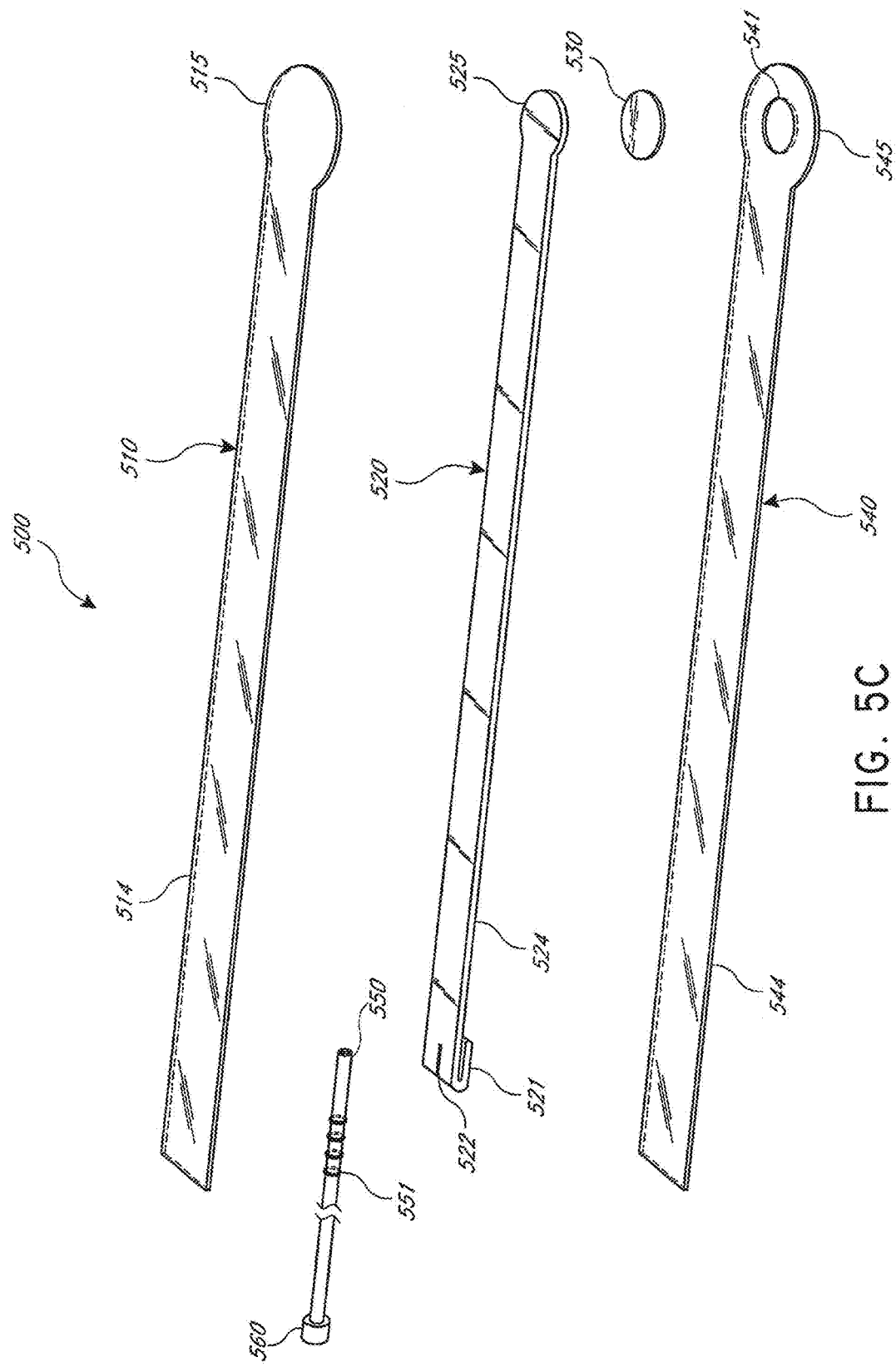
FIG. 5C illustrates a perspective exploded view of an embodiment of a flexible fluidic connector.

FIGS. 5A-B illustrate an embodiment of a flexible port or fluidic connector 500. FIG. 5C illustrates a perspective exploded view the fluidic connector 500 that may be used to connect a wound dressing to a source of negative pressure. The fluidic connector 500 comprises a top layer 510, a spacer layer 520, a filter element 530, a bottom layer 540, and a conduit 550. The conduit optionally comprises a coupling 560. In some embodiments the conduit may comprise a fluidic connector. It is expressly contemplated that a conduit may be a soft bridge, a hard tube, or any other apparatus which may serve to transport fluid. The distal end of the fluidic connector 500 (the end connectable to a dressing) is depicted as having an enlarged circular shape, although it will be appreciated that any suitable shape may be used and that the distal end need not be enlarged. For example, the distal end can have any of the shapes shown in FIGS. 3A-3C above.

The bottom layer 540 may comprise an elongate bridge portion 544, an enlarged (e.g., rounded or circular) sealing portion 545, and an orifice 541. In some embodiments a plurality of orifices may be provided in the bottom layer. Some embodiments of the rounded sealing portion 545 may comprise a layer of adhesive, for example a pressure sensitive adhesive, on the lower surface for use in sealing the fluidic connector 500 to a dressing. For example, the fluidic connector may be sealed to a cover layer of the dressing. The orifice 541 in the bottom layer 540 of the port 500 may be aligned with an orifice in the cover layer of the dressing in order to transmit negative pressure through the dressing and into a wound site.

The top layer 515 may be substantially the same shape as the bottom layer in that it comprises an elongate bridge 514 and an enlarged (e.g., rounded or circular) portion 545. The top layer 515 and the bottom layer 545 may be sealed together, for example by heat welding. In some embodiments, the bottom layer 545 may be substantially flat and the top layer 515 may be slightly larger than the bottom layer 545 in order to accommodate the height of the spacer layer 520 and seal to the bottom layer 545. In other embodiments, the top layer 515 and bottom layer 3145 may be substantially the same size, and the layers may be sealed together approximately at the middle of the height of the spacer layer 520. In some embodiments, the elongate bridge portions 544, 514 may have a length of 10 cm (or about 10 cm) or more, more preferably a length of 20 cm (or about 20 cm) or more and in some embodiments, may be about 69 cm (or 27 cm) long. Some embodiments of the entire fluidic connector, from a proximal-most edge of the top and bottom layers to a distal-most edge of the top and bottom layers, may be between 20 cm and 80 cm (or about 20 cm to about 80 cm) long, more preferably about 60 cm and 80 cm (or between about 60 cm and about 80 cm) long, for example about 70 cm long. In some embodiments, the elongate bridge portions may have a width of between 1 cm and 4 cm (or between about 1 cm and about 4 cm), and in one embodiment, is about 2.5 cm wide. The ratio of the length of the elongate bridge portions 544, 514 to their widths may in some embodiments exceed 6:1, and may more preferably exceed 8:1 or even 10:1. The diameter of the circular portion 545, 515 may be about 3.5 cm in some embodiments.

The bottom and top layers may comprise at least one layer of a flexible film, and in some embodiments may be transparent. Some embodiments of the bottom layer 540 and top layer 515 may be polyurethane, and may be liquid impermeable.

The fluidic connector 500 may comprise a spacer layer 520, such as the 3D fabric discussed above, positioned between the lower layer 540 and the top layer 510. The spacer layer 520 may be made of any suitable material, for example material resistant to collapsing in at least one direction, thereby enabling effective transmission of negative pressure therethrough. Instead of or in addition to the 3D fabric discussed above, some embodiments of the spacer layer 520 may comprise a fabric configured for lateral wicking of fluid, which may comprise viscose, polyester, polypropylene, cellulose, or a combination of some or all of these, and the material may be needle-punched. Some embodiments of the spacer layer 520 may comprise polyethylene in the range of 40-160 grams per square meter (gsm) (or about 40 to about 160 gsm), for example 80 (or about 80) gsm. Such materials may be constructed so as to resist compression under the levels of negative pressure commonly applied during negative pressure therapy.

The spacer layer 520 may comprise an elongate bridge portion 524, an enlarged (e.g., rounded or circular) portion 525, and may optionally include a fold 521. In some embodiments, the elongate bridge portion may have dimensions in the same ranges as the bridge portions of the upper and lower layers described above though slightly smaller, and in one embodiment is about 25.5 cm long and 1.5 cm wide. Similarly, the diameter of the circular portion 525 may be slightly smaller than the diameters of the enlarged ends 545, 515, and in one embodiment is about 2 cm. Some embodiments of the spacer layer 520 may have adhesive on one or both of its proximal and distal ends (e.g., one or more dabs of adhesive) in order to secure the spacer layer 520 to the top layer 510 and/or the bottom layer 540. Adhesive may also be provided along a portion or the entire length of the spacer layer. In other embodiments, the spacer layer 520 may be freely movable within the sealed chamber of the top and bottom layers.

The fold 521 of the spacer layer may make the end of the fluidic connector 500 softer and therefore more comfortable for a patient, and may also help prevent the conduit 550 from blockage. The fold 521 may further protect the end of the conduit 550 from being occluded by the top or bottom layers. The fold 521 may, in some embodiments, be between 1 cm and 3 cm (or between about 1 cm and about 3 cm) long, and in one embodiment is 2 cm (or about 2 cm) long. The spacer layer may be folded underneath itself that is toward the bottom layer 540, and in other embodiments may be folded upward toward the top layer 510. Other embodiments of the spacer layer 520 may contain no fold. A slot or channel 522 may extend perpendicularly away from the proximal end of the fold 521, and the conduit 550 may rest in the slot or channel 522. In some embodiments the slot 522 may extend through one layer of the fold, and in others it may extend through both layers of the fold. The slot 522 may, in some embodiments, be 1 cm (or about 1 cm) long. Some embodiments may instead employ a circular or elliptical hole in the fold 521. The hole may face proximally so that the conduit 550 may be inserted into the hole and rest between the folded layers of spacer fabric. In some embodiments, the conduit 550 may be adhered to the material of the fold 521, while in other embodiments it may not.

The fluidic connector 500 may have a filter element 530 located adjacent the orifice 541, and as illustrated is located between the lower layer 540 and the spacer layer 520. The filter element 530 may be positioned across the opening or orifice of the fluidic connector 500. The filter element 530 is impermeable to liquids, but permeable to gases. The filter element may be similar to the element described above with respect to FIG. 1B, and as illustrated may have a round or disc shape. The filter element 530 can act as a liquid barrier, to substantially prevent or inhibit liquids from escaping from the wound dressing, as well as an odor barrier. The filter element 530 may also function as a bacterial barrier. In some embodiments, the pore size of the filter element 530 can be approximately 0.2 µm. Suitable materials for the filter material of the filter element include 0.2 micron Gore™ expanded PTFE from the MMT range, PALL Versapore™ 200R, and Donaldson™ TX6628. The filter element 530 thus enables gas to be exhausted through the orifice. Liquid, particulates and pathogens however are contained in the dressing. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. In some embodiments, the filter element 530 may be adhered to one or both of top surface of the bottom layer 540 and the bottom surface of the spacer layer 520 using an adhesive such as, but not limited to, a UV cured adhesive. In other embodiments, the filter 530 may be welded to the inside of the spacer layer 520 and to the top surface of the bottom layer 540. The filter may also be provided adjacent the orifice on a lower surface of the bottom layer 540. Other possible details regarding the filter are disclosed in U.S. Patent Pub. No. 2011/0282309 and incorporated by reference herein.

The proximal end of the fluidic connector 500 may be connected to the distal end of a conduit 550. The conduit 550 may comprise one or more circular ribs 551. The ribs 551 may be formed in the conduit 550 by grooves in a mold during the manufacturing of the conduit. During heat welding of the upper and lower layers 515, 545 melted material from those layers may flow around the ribs 551, advantageously providing a stronger connection between the conduit 550 and the layers. As a result, it may be more difficult to dislodge the conduit 550 out from between the layers during use of the fluidic connector 500.

The proximal end of the conduit 550 may be optionally attached to a coupling 560. The coupling 560 may be used to connect the fluidic connector 500 to a source of negative pressure, or in some embodiments to an extension conduit which may in turn be connected to a source of negative pressure. As explained in more detail below with respect to FIGS. 8A and 8B, the proximal end of the conduit 550, which is inserted into the spacer fabric 520, may be shaped in such a way to reduce the possibility of occlusion. For example, some embodiments may have a triangular portion cut out of the end of the conduit, and other embodiments may have a plurality of holes therethrough.

Figure 6:
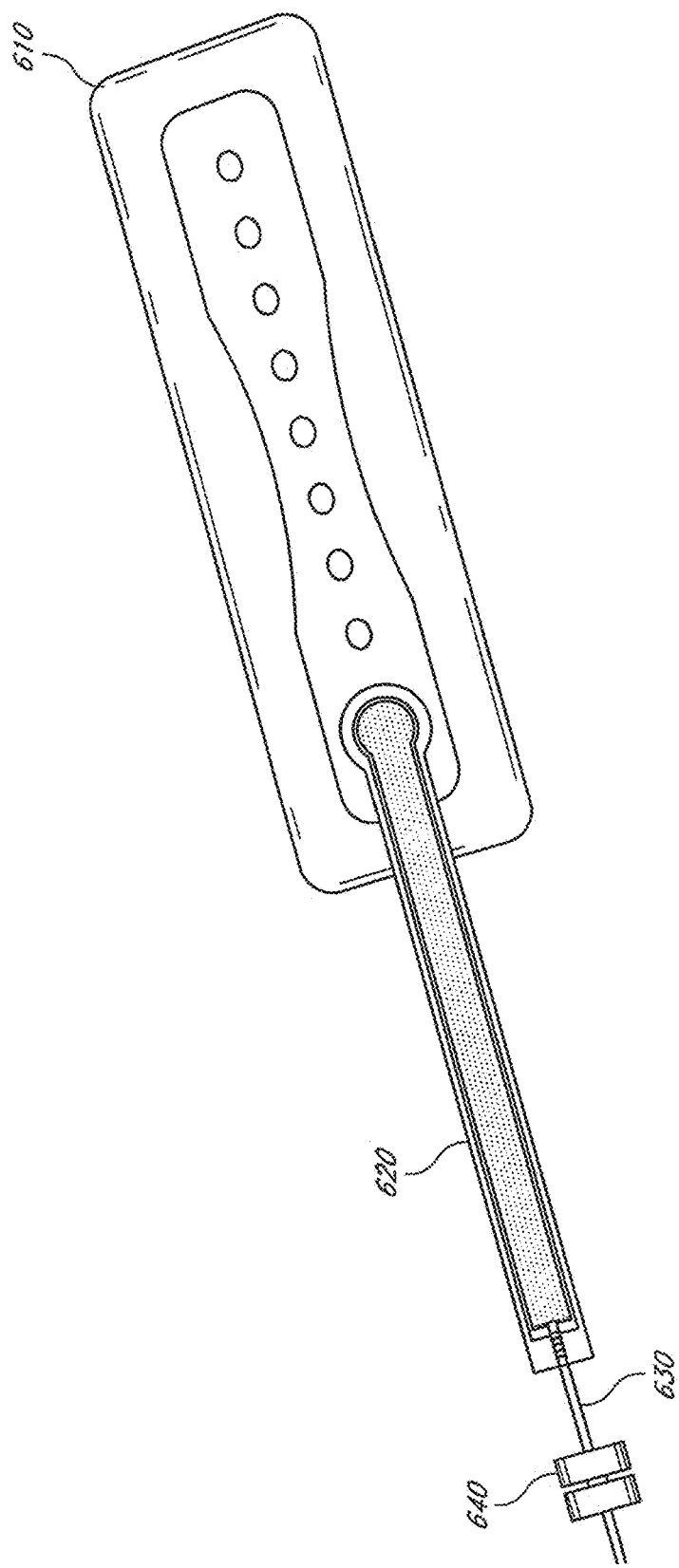
FIG. 6 illustrates an embodiment of a flexible fluidic connector attached to a wound dressing.

FIG. 6 illustrates an embodiment of a wound dressing 610 with a fluidic connector 620 such as described above with respect to FIGS. 5A-C attached to the dressing. The fluidic connector 620 may be the fluidic connector described above in FIGS. 5A-C. The fluidic connector 620 may comprise a conduit 630 and a coupling 640 for connecting the fluidic connector to a source of negative pressure or to an extension conduit. Although in this depiction the fluidic connector 620 is connected over a circular window in the obscuring layer of the dressing 610, in other embodiments the fluidic connector 620 may be connected over a maltese cross in the obscuring layer. In some embodiments, the maltese cross may be of a larger diameter than the fluidic connector 620 and may be at least partially viewable after the fluidic connector 620 is attached to the dressing 610. Further details regarding the dressing 610 and other dressings to which the fluidic connector can be connected are described in International Patent Publications WO2012020440 and WO2014020443, the entireties of which are hereby incorporated by reference.

FIG. 7A depicts a perspective view of a flexible fluidic connector 700 of the same design as shown with respect to FIGS. 5A-C. The fluidic connector 700 comprises spacer fabric 710, wherein the proximal end of spacer fabric 710 comprises a fold 720, at least one layer of flexible film 740, an enlarged rounded distal end 715 providing the sealing surface that is applied to a wound dressing, a conduit 760, and a coupling 780. The components of fluidic connector 700 may have similar properties to the components of FIGS. 5A-C, described above.

FIG. 7B illustrates a close up view of an embodiment of the proximal end of the flexible fluidic connector 700. The fluidic connector 700 comprises spacer fabric 710 inside a sealed chamber 770 between layers of flexible film 740. The end of the spacer fabric 710 comprises a fold 720. At the proximal end of the fold, there may be a hole 730 through the fabric for inserting the conduit 760. The conduit 760 may rest between the folded portions of the spacer fabric. The conduit 760 comprises a plurality of ribs 750, which may, as described above with respect to FIGS. 5A-C, act to secure the conduit 760 between the layers of flexible film 740.

FIG. 7C illustrates a close up view of the bottom of the distal end of the flexible fluidic connector 700. The bottom of the fluidic connector 700 comprises an orifice 792 for transmitting negative pressure to a dressing to which the fluidic connector may be attached. The fluidic connector 700 comprises a filter 790, which may have similar properties to the filters described above with respect to FIGS. 5A-C. In some embodiments, the filter 790 may have a portion 795 which is adhered to the flexible film 740 around the perimeter of the orifice 795, thereby substantially maintaining the seal of chamber 770.

Figure 8A:
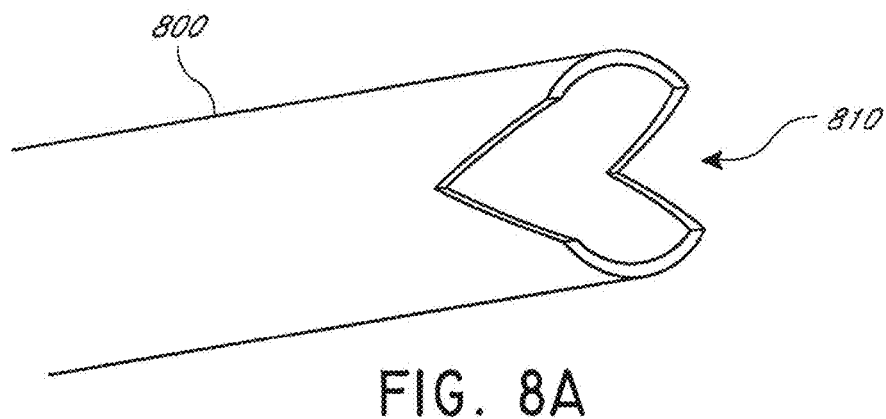
FIGS. 8A-B illustrate various embodiments of the distal end of a conduit which may be part of a flexible fluidic connector.
Figure 8B:
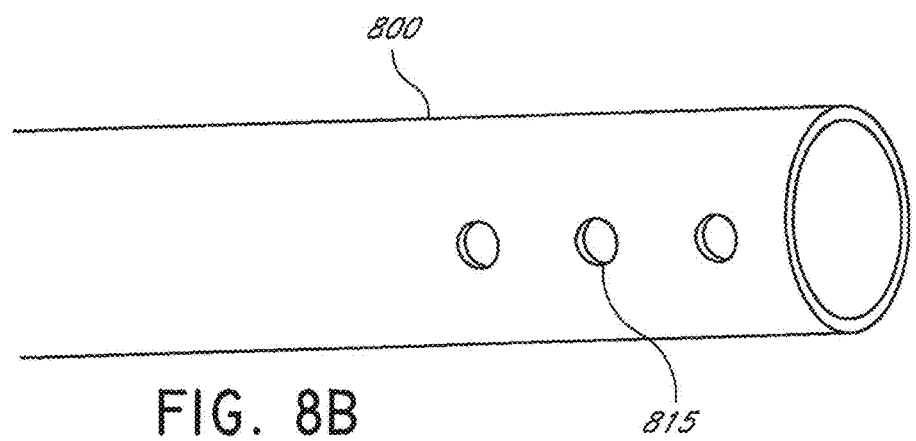
Figure 9:
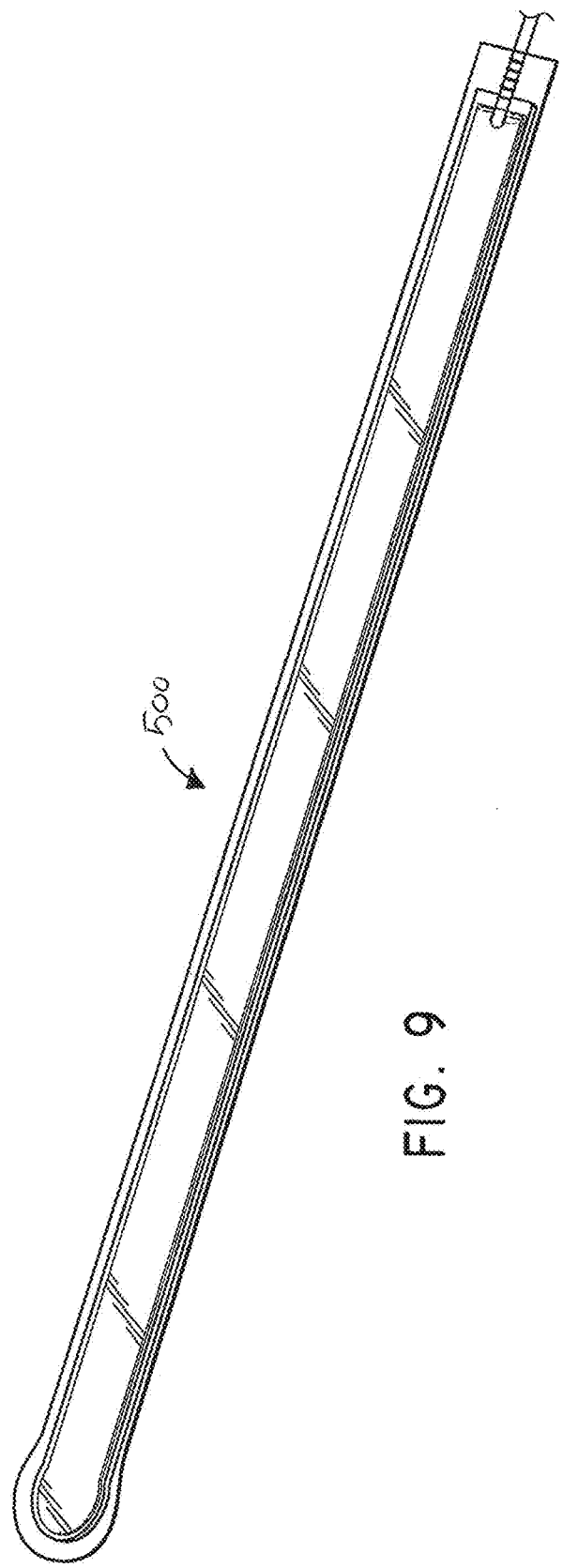
FIG. 9 illustrates a perspective top view of an ornamental design of one embodiment of a flexible fluidic connector as disclosed herein.
Figure 10:
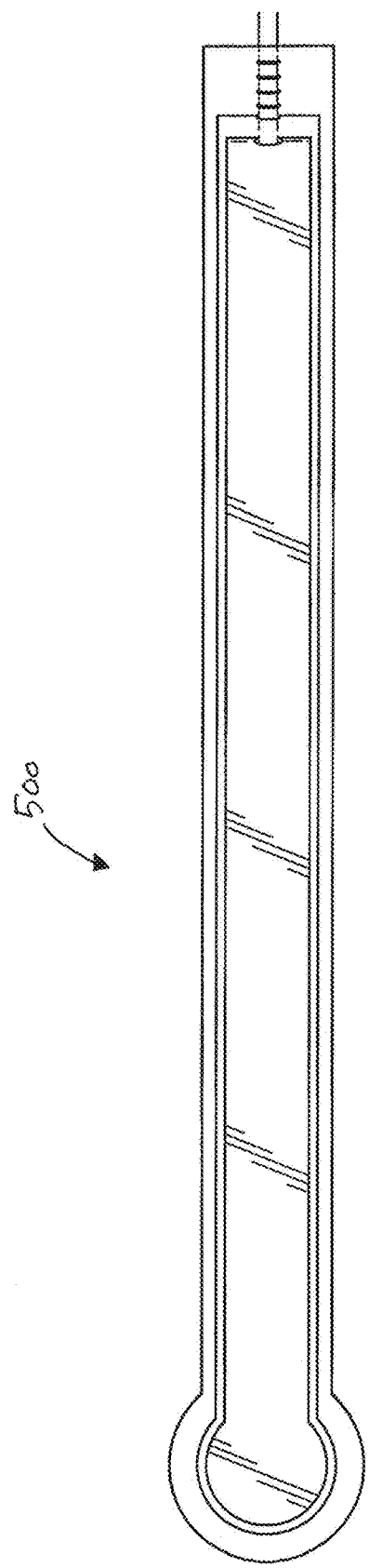
FIG. 10 illustrates a top plan view of the flexible fluidic connector of FIG. 9.
Figure 11:
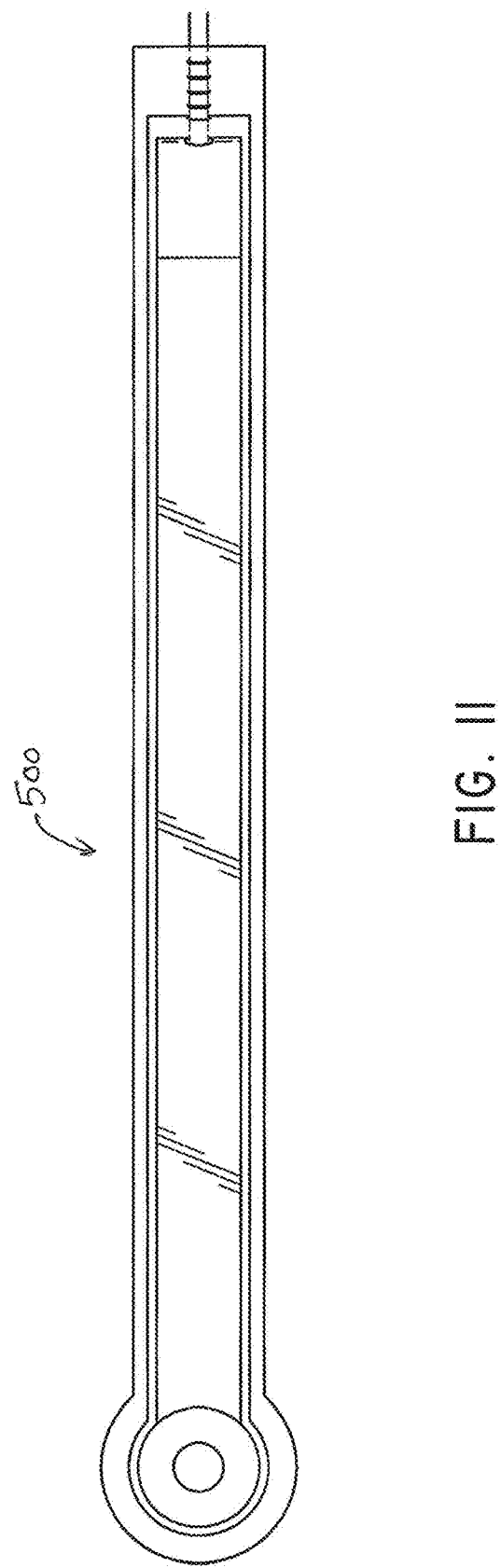
FIG. 11 illustrates a bottom view of the flexible fluidic connector of FIG. 9.
Figure 12:
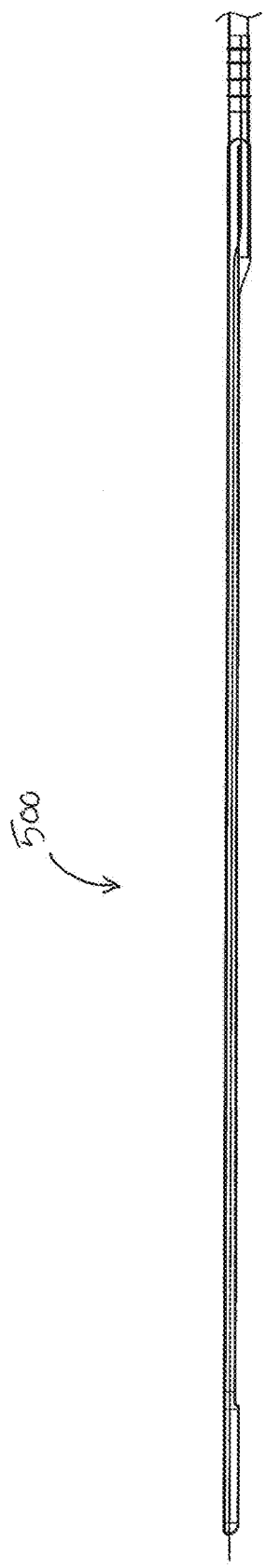
FIG. 12 is a far side view of the flexible fluidic connector of FIG. 9.
Figure 13:
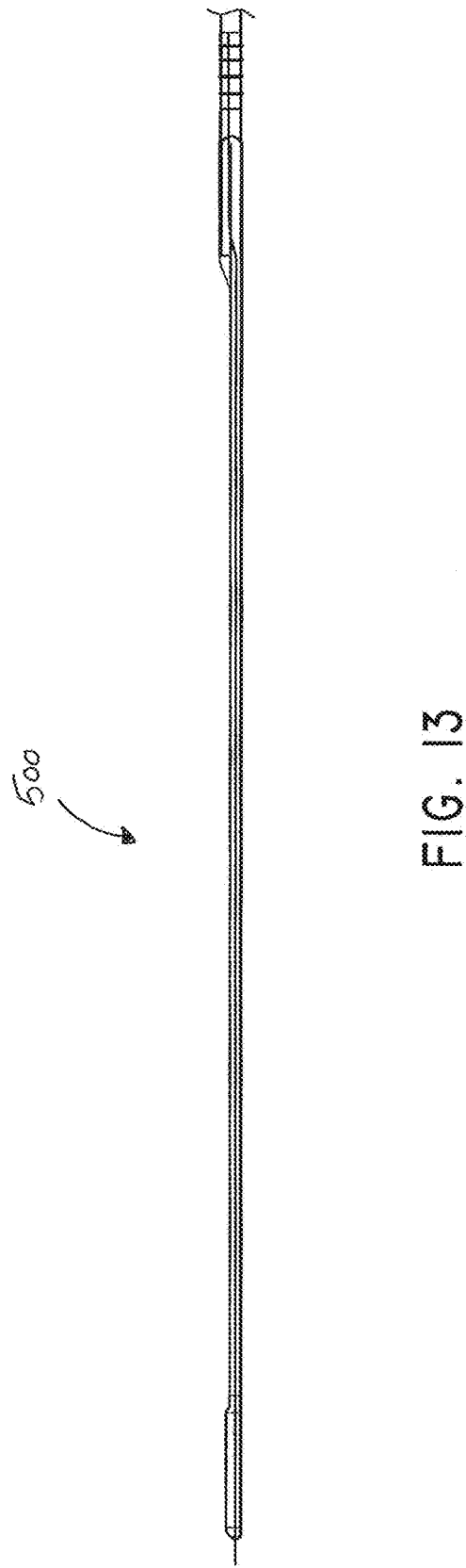
FIG. 13 is a near side view of the flexible fluidic connector of FIG. 9.
Figure 14:
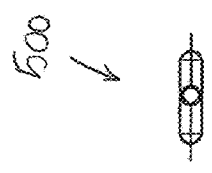
FIG. 14 is a front view of the flexible fluidic connector of FIG. 9.
Figure 15:
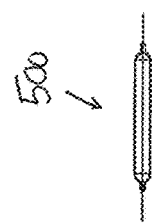
FIG. 15 is a rear view of the flexible fluidic connector of FIG. 9.

FIGS. 8A and 8B illustrate embodiments of the distal end of a conduit 800 which may be part of any of the fluidic connector embodiments described above. The distal end may be shaped in such a way to reduce the possibility of occlusion. For example, the embodiment of FIG. 8A may have a triangular portion 810 cut out of the end of the conduit, and other embodiments may have a plurality of holes therethrough.

FIGS. 9-16 depict various views of an ornamental design of one embodiment of a flexible fluidic connector 500 as described herein. As will be evident from the various embodiments described herein, functionally equivalent alternative designs of such a flexible fluidic connector are available, and the configuration of the design illustrated in FIGS. 9-16 was at least in part the result of aesthetic and ornamental considerations. In the case of the illustrated full flexible fluidic connector design, the solid lines indicate the incorporation of the entire structure as part of one embodiment of an ornamental design for the flexible fluidic connector. In the case of a partial flexible port design, any number of the solid lines may instead be depicted as broken lines to indicate that a component illustrated in broken lines is not part of that embodiment of the ornamental design.

Figure 17:
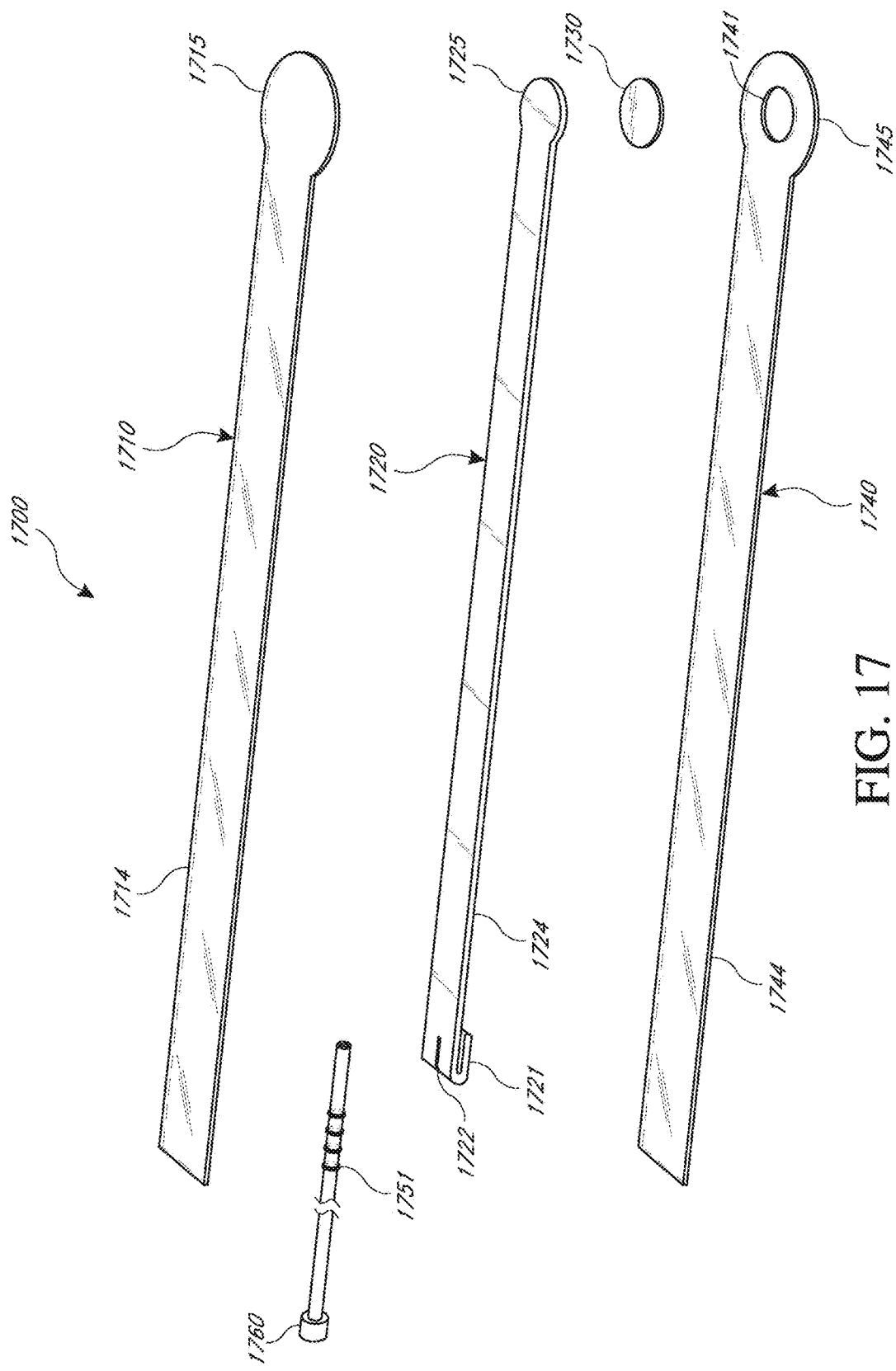
FIG. 17 illustrates an exploded view of an embodiment of a soft or flexible fluidic connector for transmitting negative pressure to a wound dressing.

FIG. 17 illustrates a perspective exploded view, like that of FIG. 5C, of an embodiment of a flexible port or fluidic connector 1700 that may be used to connect a wound dressing, for example a wound dressing as described in International Patent Publication WO2013175306, which is hereby incorporated by reference in its entirety, to a source of negative pressure. The fluidic connector 1700 comprises a top layer 1710, a spacer layer 1720, a filter element 1730, a bottom layer 1740, and a conduit 1750. The conduit optionally comprises a coupling 1760. The distal end of the fluidic connector 1700 (the end connectable to the dressing B310) is depicted as having an enlarged circular shape, although it will be appreciated that any suitable shape may be used and that the distal end need not be enlarged. For example, the distal end can have any of the shapes shown FIGS. 3A-3C above.

The bottom layer 1740 may comprise an elongate bridge portion 1744, an enlarged (e.g., rounded or circular) sealing portion 1745, and an orifice 1741. In some embodiments a plurality of orifices may be provided in the bottom layer. Some embodiments of the rounded sealing portion 1745 may comprise a layer of adhesive, for example a pressure sensitive adhesive, on the lower surface for use in sealing the fluidic connector 1700 to a dressing. The orifice 1741 in the bottom layer 1740 of the port 1700 may be aligned with an orifice in the cover layer of a dressing in order to transmit negative pressure through the dressing and into a wound site. In some embodiments the wound dressing may be substantially identical to the dressing as described in International Patent Publication WO2013175306, which is incorporated by reference in its entirety.

The top layer 1715 may be substantially the same shape as the bottom layer in that it comprises an elongate bridge 1714 and an enlarged (e.g., rounded or circular) portion 1715. The top layer 1715 and the bottom layer 1745 may be sealed together, for example by heat welding. In some embodiments, the bottom layer 1745 may be substantially flat and the top layer 1715 may be slightly larger than the bottom layer 1745 in order to accommodate the height of the spacer layer 1720 and seal to the bottom layer 1745. In other embodiments, the top layer 1715 and bottom layer 1745 may be substantially the same size, and the layers may be sealed together approximately at the middle of the height of the spacer layer 1720. In some embodiments, the elongate bridge portions 1744, 1714 may have a length of 10 cm (or about 10 cm) or more, more preferably a length of 20 cm (or about 20 cm) or more and in some embodiments, may be about 27 cm long. In some embodiments, the elongate bridge portions may have a width of between 1 cm and 4 cm (or between about 1 cm and about 4 cm), and in one embodiment, is about 2.5 cm wide. The ratio of the length of the elongate bridge portions 1744, 1714 to their widths may in some embodiments exceed 6:1, and may more preferably exceed 8:1 or even 10:1. The diameter of the circular portion 1745, 1715 may be about 3.5 cm in some embodiments.

The bottom and top layers may comprise at least one layer of a flexible film, and in some embodiments may be transparent. Some embodiments of the bottom layer 1740 and top layer 1715 may be polyurethane, and may be liquid impermeable.

The fluidic connector 1700 may comprise a spacer layer 1720, such as the 3D fabric discussed above, positioned between the lower layer 1740 and the top layer 1710. The spacer layer 1720 may be made of any suitable material, for example material resistant to collapsing in at least one direction, thereby enabling effective transmission of negative pressure therethrough. The spacer layer 1720 may comprise an enlarged (e.g., rounded or circular) portion 1725, and may optionally include a fold 1721. In some embodiments, the elongate bridge portion may have dimensions in the same ranges as the bridge portions of the upper and lower layers described above though slightly smaller, and in one embodiment is about 25.5 cm long and 1.5 cm wide. Similarly, the diameter of the circular portion 1725 may be slightly smaller than the diameters of the enlarged ends 1745, 1715, and in one embodiment is about 2 cm. Some embodiments of the spacer layer 1720 may have adhesive on one or both of its proximal and distal ends (e.g., one or more dabs of adhesive) in order to secure the spacer layer 1720 to the top layer 1710 and/or the bottom layer 1740. Adhesive may also be provided along a portion or the entire length of the spacer layer. In other embodiments, the spacer layer 1720 may be freely movable within the sealed chamber of the top and bottom layers.

The fold 1721 of the spacer fabric may make the end of the fluidic connector 1700 softer and therefore more comfortable for a patient, and may also help prevent the conduit 1750 from blockage. The fold 1721 may further protect the end of the conduit 1750 from being occluded by the top or bottom layers. The fold 1721 may, in some embodiments, be between 1 cm and 3 cm (or between about 1 cm and about 3 cm) long, and in one embodiment is 2 cm (or about 2 cm) long. The spacer fabric may be folded underneath itself, that is toward the bottom layer 1740, and in other embodiments may be folded upward toward the top layer 1710. Other embodiments of the spacer layer 1720 may contain no fold. A slot or channel 3522 may extend perpendicularly away from the proximal end of the fold 1721, and the conduit 1750 may rest in the slot or channel 1722. In some embodiments the slot 1722 may extend through one layer of the fold, and in others it may extend through both layers of the fold. The slot 1722 may, in some embodiments, be 1 cm (or about 1 cm) long. Some embodiments may instead employ a circular or elliptical hole in the fold 1721. The hole may face proximally so that the conduit 1750 may be inserted into the hole and rest between the folded layers of spacer fabric. In some embodiments, the conduit 1750 may be adhered to the material of the fold 1721, while in other embodiments it may not.

The fluidic connector 1700 may have a filter element 1730 located adjacent the orifice 1741, and as illustrated is located between the lower layer 1740 and the spacer layer 1720. As illustrated, the filter element 1730 may have a round or disc shape. The filter element 1730 is impermeable to liquids, but permeable to gases. The filter element 1730 can act as a liquid barrier, to substantially prevent or inhibit liquids from escaping from the wound dressing, as well as an odor barrier. The filter element 1730 may also function as a bacterial barrier. In some embodiments, the pore size of the filter element 1730 can be approximately 0.2 µm. Suitable materials for the filter material of the filter element include 0.2 micron Gore™ expanded PTFE from the MMT range, PALL Versapore™ B200R, and Donaldson™ TX6628. The filter element 1730 thus enables gas to be exhausted through the orifice. Liquid, particulates and pathogens however are contained in the dressing. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. In some embodiments, the filter element 1730 may be adhered to one or both of top surface of the bottom layer 1740 and the bottom surface of the spacer layer 1720 using an adhesive such as, but not limited to, a UV cured adhesive. In other embodiments, the filter 1730 may be welded to the inside of the spacer layer 1720 and to the top surface of the bottom layer 1740. The filter may also be provided adjacent the orifice on a lower surface of the bottom layer 1740. Other possible details regarding the filter are disclosed in U.S. Patent Pub. No. 2011/0282309 which is incorporated by reference herein.

The proximal end of the fluidic connector 1700 may be connected to the distal end of a conduit 1750. The conduit 1750 may comprise one or more circular ribs 1751. The ribs 1751 may be formed in the conduit 1750 by grooves in a mold during the manufacturing of the conduit. During heat welding of the upper and lower layers 1715, 1745 melted material from those layers may flow around the ribs 1751, advantageously providing a stronger connection between the conduit 1750 and the layers. As a result, it may be more difficult to dislodge the conduit 1750 out from between the layers during use of the fluidic connector 1700.

The proximal end of the conduit 1750 may be optionally attached to a coupling 1760. The coupling 1760 may be used to connect the fluidic connector 1700 to a source of negative pressure, or in some embodiments to an extension conduit which may in turn be connected to a source of negative pressure. The distal end of the conduit 1750, which is inserted into the spacer layer 1720, may be shaped in such a way to reduce the possibility of occlusion.

Figure 18:
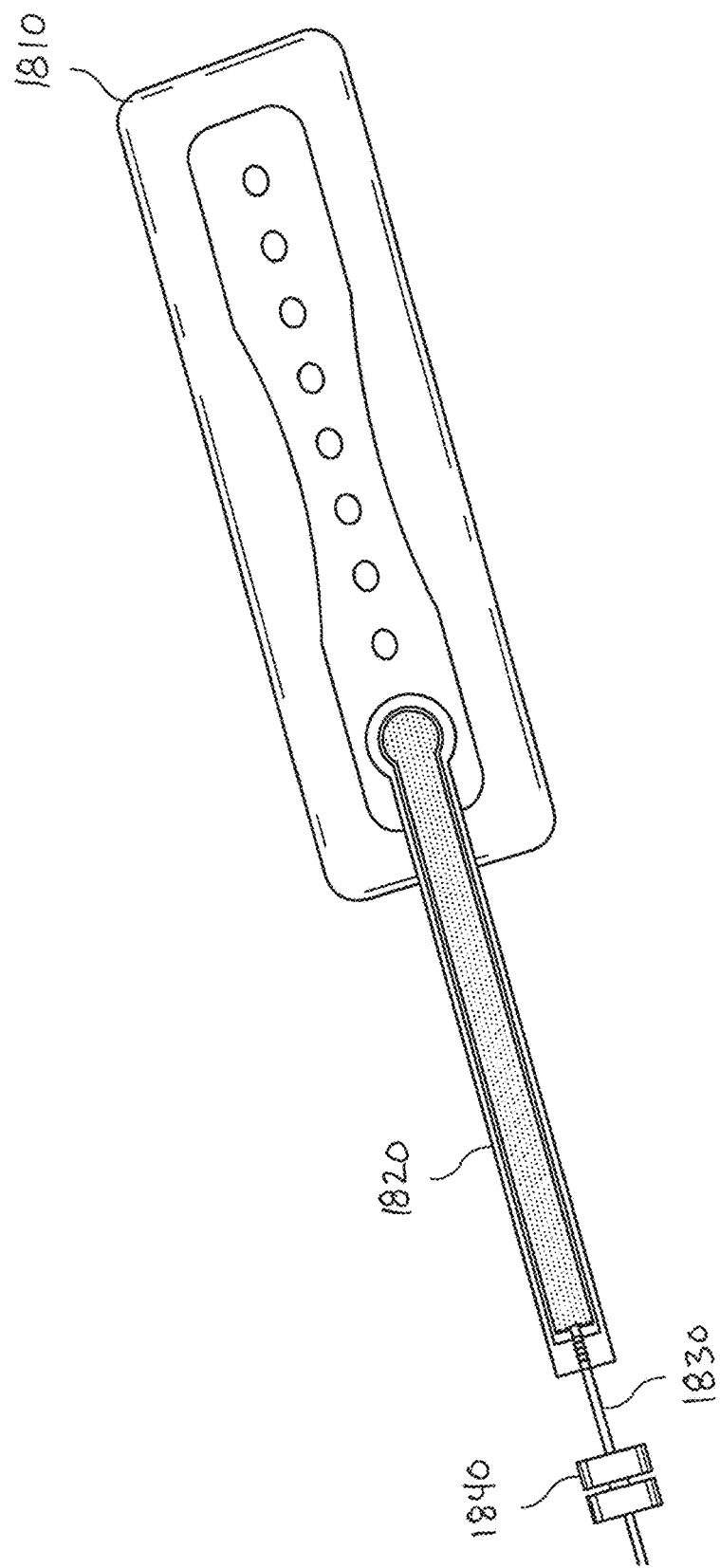
FIG. 18 illustrates an embodiment of a soft or flexible fluidic connector attached to a wound dressing.

FIG. 18 illustrates an embodiment of a wound dressing 1810 with a flexible fluidic connector 1820 such as described with respect to FIG. 17 above. The fluidic connector 1820 comprises a conduit 1830 and a coupling 1840 for connecting the port to a source of negative pressure or to an extension conduit. The dressing 1810 comprises an obscuring layer with one row of eight holes in a linear arrangement. Although in this depiction the fluidic connector 1820 is connected over a circular window in the obscuring layer of the dressing 1810, in other embodiments the fluidic connector 1820 may be connected over a maltese cross in the obscuring layer. In some embodiments, the maltese cross may be of a larger diameter than the port and may be at least partially viewable after the port is attached to the dressing.

As introduced above, problems may arise when a fluidic connector or suction port adhered to a top surface of a wound dressing is pulled away from the dressing. For example, a fluidic connector may be adhered to the top surface of a wound dressing via an applicator or sealing surface, as described herein above. The applicator may be adhered to the cover layer of the dressing by an adhesive, such as an adhesive ring. When the applicator is compressed to the dressing top surface with the adhesive in between, localized peaks of adhesive may form. Where the fluidic connector is adhered to the top layer of the wound dressing, an elongate conduit such as the bridge described above, or a length of tubing coupled to a proximal end of the fluidic connector, may extend away from the applicator in a direction parallel or substantially parallel with the top surface of the dressing. If the fluidic connector or elongate conduit is pulled in certain directions, the localized peaks of adhesive may create areas of intense stress concentration which can lead to pin holing in the dressing after a small tug, which can cause undesirable leaks. Additionally, in some instances the tubing or conduit coupled to the fluidic connector may be bent backwards 180° during use such that a small tug can cause peeling of the fluidic connector away from the dressing.

Figure 19A:
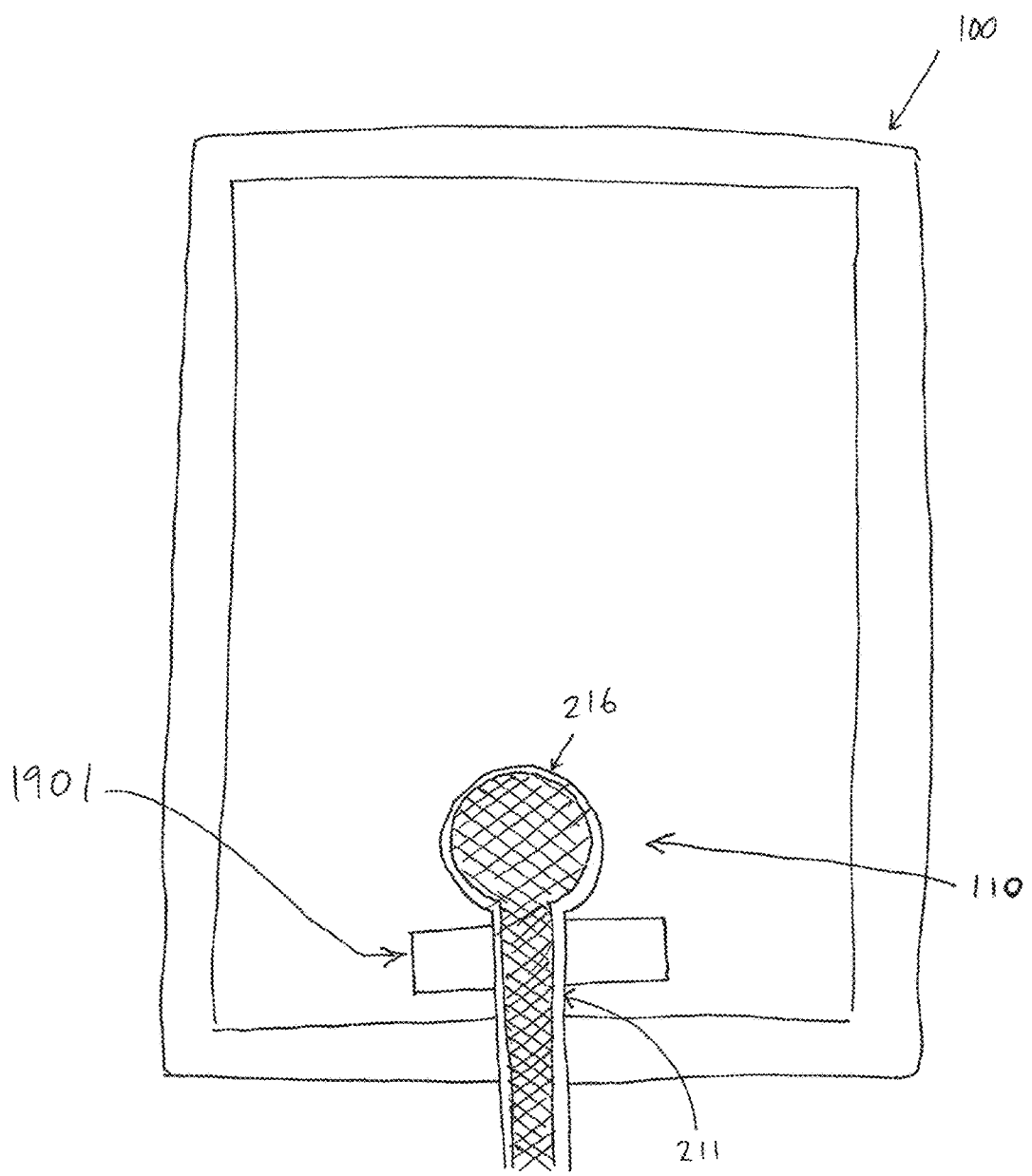
FIG. 19A illustrates a top view of a negative pressure wound treatment system employing a wound dressing and a fluidic connector with a reinforcement.
Figure 19B:
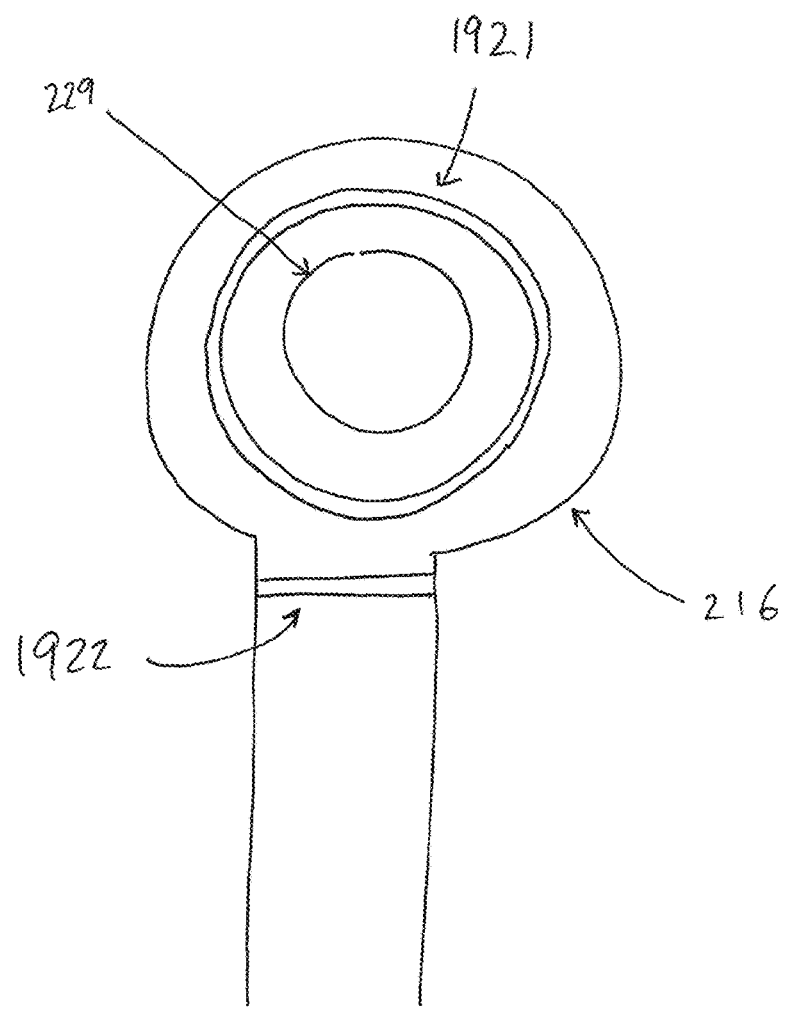
FIG. 19B illustrates a bottom view of an embodiment of flexible fluidic connector.
Figure 19C:
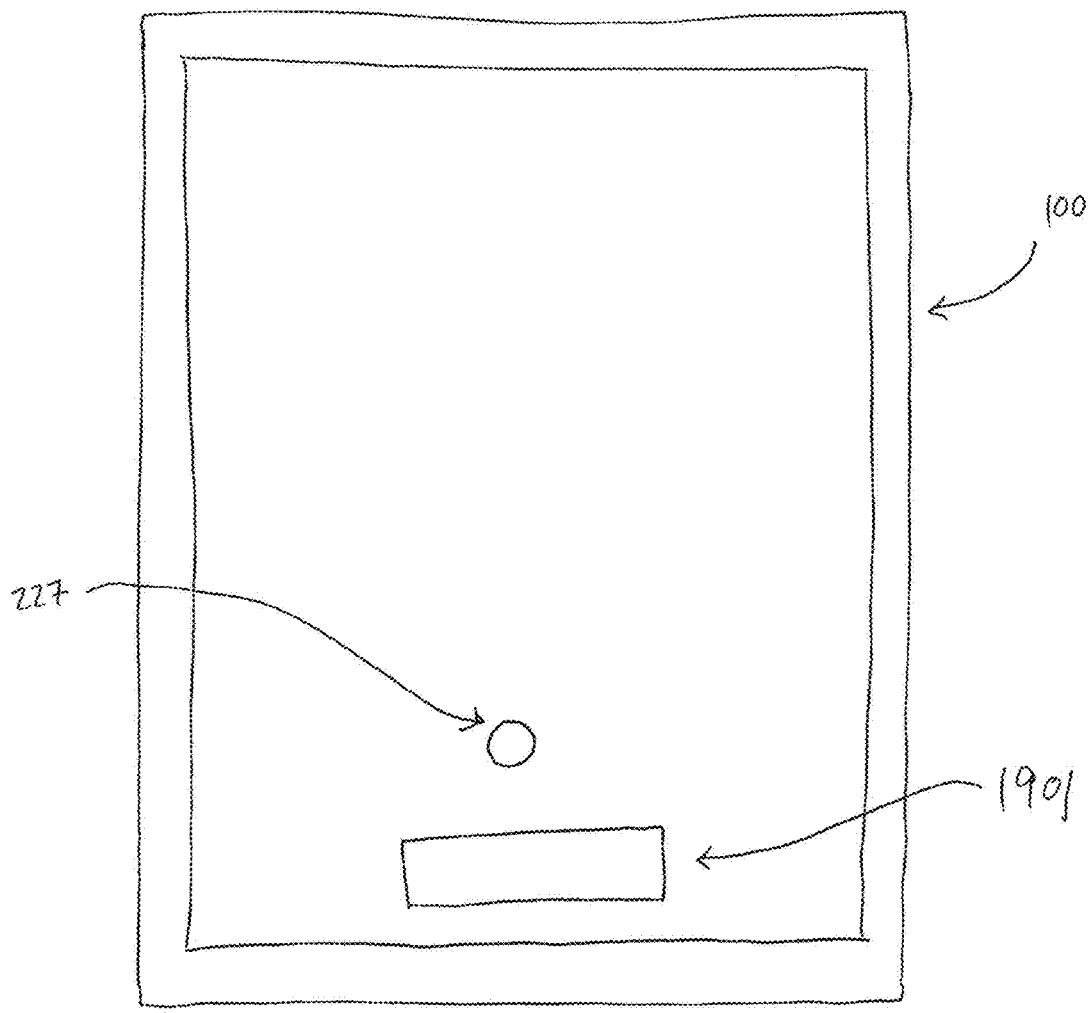
FIG. 19C illustrates a top view of a wound dressing and a reinforcement of an embodiment of a negative pressure wound treatment system.

FIGS. 19A-C illustrate another embodiment of a wound treatment apparatus comprising a reinforcement for use with a fluidic connector. The fluidic connector 110 may be similar to the fluidic connectors described above with respect to FIGS. 1-18. As shown in FIG. 19A, a reinforcement 1901 may be located under the elongate bridge 211 of the fluidic connector 110. The reinforcement 110 may alternatively or additionally be located under part or all of the sealing surface 216. In some embodiments the reinforcement 1901 comprises a strip of flexible film or patch. Although the reinforcement is depicted as rectangular, the reinforcement may comprise other shapes.

The reinforcement 1901 may comprise any suitable high strength flexible film, tape or fabric such that when adhered to the wound dressing 100, the fluidic connector 110 is able to withstand a pull force of about 15N without creating pinholes in the top layer of the wound dressing 100. The reinforcement 1901 may comprise a polymer or plastic material such as polyurethane (PU), polyethylene terephthalate (PET), Nylon, or PVCI. The reinforcement 1901 may alternatively comprise polyethylene (PE) or polypropylene (PP) where an appropriate adhesive is used with the reinforcement. The reinforcement may comprise a polymer film or a woven or non-woven fabric material.

The reinforcement 1901 may further comprise an adhesive on the lower, wound-facing surface for use in sealing the reinforcement to a wound dressing. The adhesive may be, for example a pressure sensitive adhesive, or a UV curable adhesive such as Loctite 4011-SG adhesive. In certain embodiments the relative stiffness of the reinforcement 1901 compared to the top layer of the wound dressing 100 or sealing surface of the fluidic connector may allow for an even coating of adhesive to be applied to the reinforcement. An even coating of adhesive may not comprise sharp outcrop or peaks, and may be a substantially uniform coating of adhesive. The adhesive coating may cover substantially the entire lower surface of the reinforcement 1901. In other embodiments, a separate adhesive or glue layer may be applied to either the wound dressing 100 or the reinforcement 1901 prior to adhering the reinforcement 1901 to the wound dressing 100. Further, the elongate bridge 211 and/or the sealing surface 216 of the fluidic connector 110 may also comprise an adhesive for use in sealing the fluidic connector to the reinforcement 1901 and the wound dressing 100.

As shown in FIG. 19B, the lower surface of the sealing surface 216 may comprise at least one aperture 229 therein to communicate with the wound dressing 110. In some embodiments the aperture 229 may be substantially the same dimensions as an aperture in the top layer of the wound dressing 100. In some embodiments the aperture may be, for example 10 mm. The lower surface of the sealing surface 216 may comprise one or more adhesive layers to adhere the sealing surface to the reinforcement 1901 and the wound dressing 100. The sealing surface 216 may in some cases be protected by an optional release layer to be removed prior to use. In some embodiments the sealing surface 216 may comprise a first adhesive layer 1921, such as in the shape of a ring, which surrounds an orifice 229 in the sealing surface, and is dimensioned so as to surround an aperture in the cover layer of the wound dressing 100. A second adhesive layer 1922 may be positioned adjacent to the first adhesive layer 1921 and the enlarged distal end of the fluidic connector. The second adhesive layer may be positioned such that it adheres the sealing surface 216 to the reinforcement 1901 when the fluidic connector is sealed to the wound dressing 100 over an orifice therein. In some embodiments the first adhesive layer 1921 and second adhesive layer 1922 may be the same adhesive. In other embodiments the first adhesive layer 1921 and second adhesive layer 1922 may be different adhesives. The adhesive or adhesives of the first adhesive layer 1921 and second adhesives layer 1922 may be separates adhesive from the adhesive which may be present on a lower surface of the reinforcement 1901.

As depicted in FIG. 19C, the reinforcement 1901 may be adhered to the top surface of a wound dressing 100 as described above. The reinforcement 1901 may be adhered to the wound dressing 100 substantially adjacent to an orifice 227 in the top surface, or backing layer of the wound dressing 100. For example, the reinforcement 1901 may be positioned overlying the absorbent layer along an edge of the wound dressing 100. As shown in FIG. 19A, the reinforcement may be positioned between the applicator or sealing surface 216 and the proximal end of the bridge of fluidic connector 110. In some alternative embodiments, the reinforcement 1901 may be adhered to the fluidic connector 110 prior to adhering the reinforcement to the wound dressing 100. In some embodiments the fluidic connector and the reinforcement are provided as an integral unit.

With reference again to FIGS. 19A-19C, the fluidic connector 1900 is positioned such that the first adhesive layer 1921 of the sealing surface 216 surrounds an orifice 227 in the cover layer of the wound dressing 100, and the second adhesive layer 1922 adheres the elongate bridge 211 of the fluidic connector to the reinforcement 1901. When the fluidic connector 110 is adhered to the reinforcement 1901 and the wound dressing 100, the first adhesive layer 1921 may act to form a seal between the sealing surface 216 and the wound dressing 100 over the orifice 227, while the second adhesive layer 1922 may act so secure the elongate bridge 211 to the reinforcement 1901. hereafter, the fluidic connector 110 may be connected to a source of negative pressure to communicate negative pressure through the fluidic connector 110 to the wound site via the wound dressing 100 as previously described herein.

The reinforcement 1901 as described above may serve to more evenly distribute the stresses applied to the top surface of a wound dressing when a fluidic connector adhered thereto is pulled away from the dressing. Rather than focusing areas of intense stress at localized peaks of adhesive, the reinforcement applies the pulling stress to a larger area of the top layer of the dressing. By distributing the pulling load over a larger area of the top layer, the risk of pin holing in the dressing after a small tug is greatly reduced.

Figure 16:
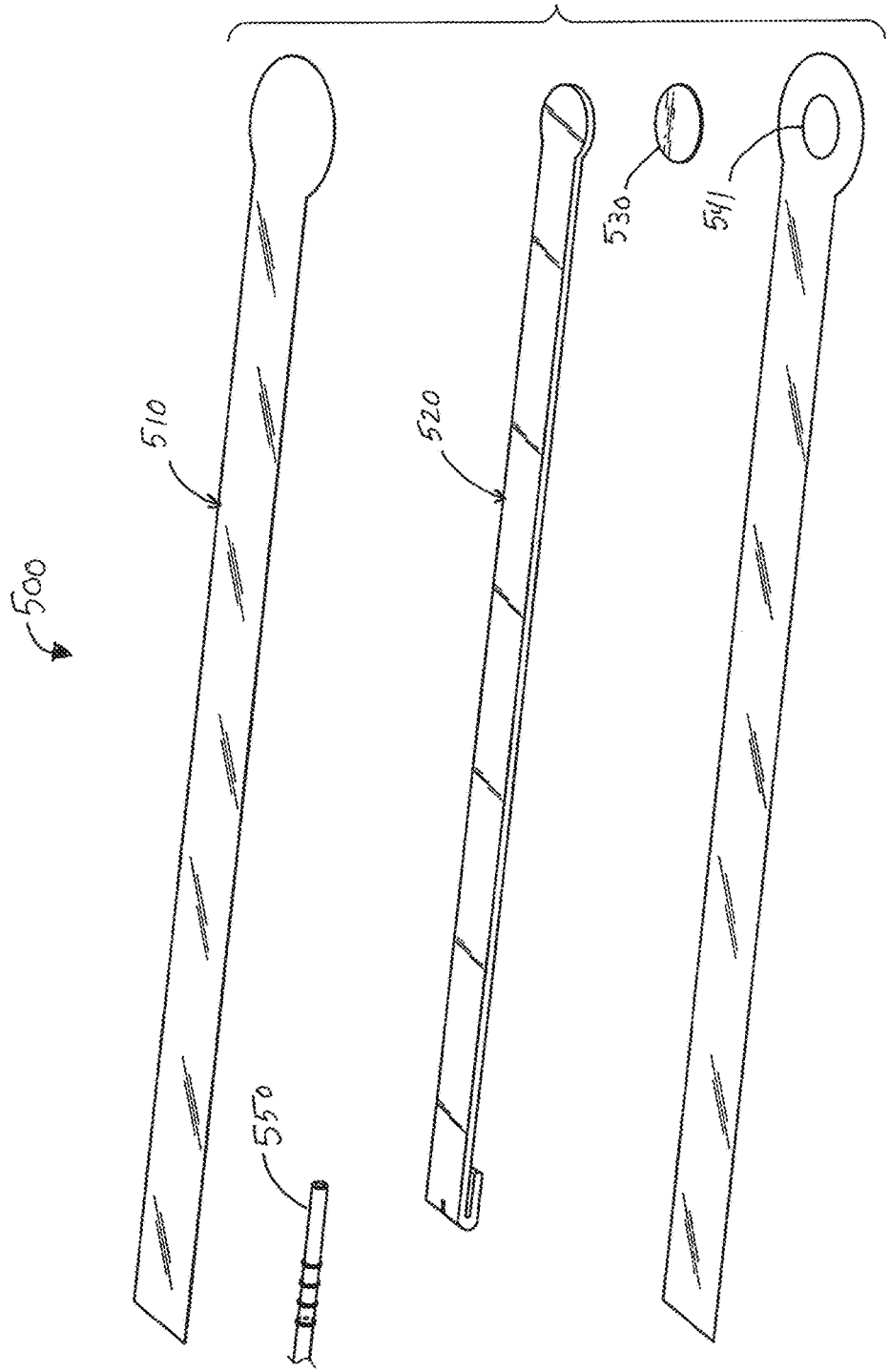
FIG. 16 is an exploded view of the flexible fluidic connector of FIG. 9.
Figure 20A:
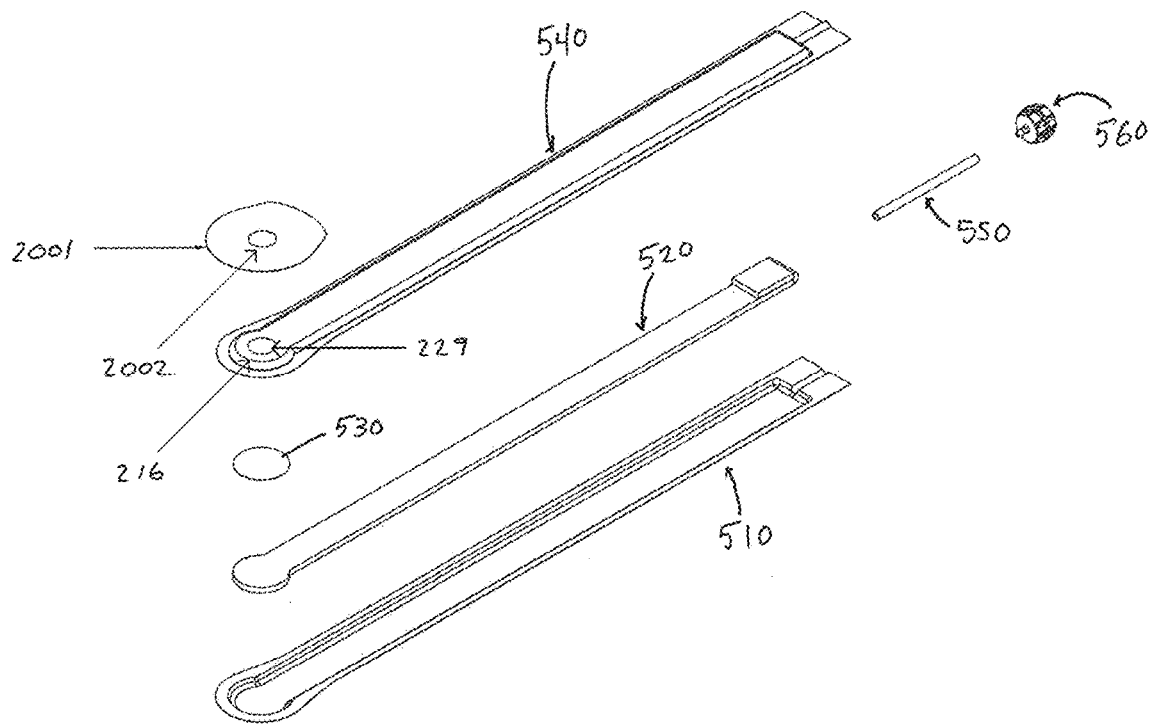
FIG. 20A illustrates an exploded view of an embodiment of a flexible fluidic connector.

FIGS. 20A-D illustrate embodiments of a reinforcement for use with a fluidic connector. The fluidic connector 110 may be similar to the fluidic connectors described above with respect to FIGS. 1-19. In the exploded view of the fluidic connector of FIG. 20A, the components are shown upside down relative to the orientation of similar components shown in earlier figures, such as shown in FIGS. 5C, 16 and 17. Reference numbers for similar components are provided in FIG. 20A to correspond with the components of FIG. 5C. Although the layers 510 and 540 in FIG. 20A are depicted as having a shape, such shapes are not necessarily preformed into the layers. Rather, these may be the shapes formed by the layer 510 and 540 due to the spacer 520 positioned therebetween.

Figure 20B:
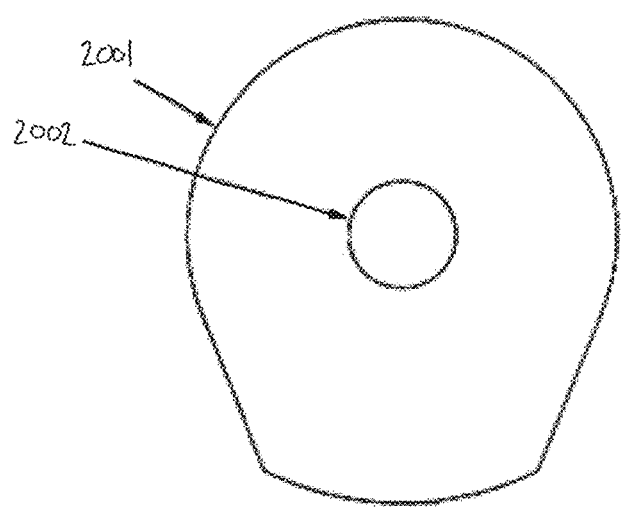
FIG. 20B illustrates a bottom view of an embodiment of a reinforcement.

As shown in FIGS. 20A-B, a reinforcement 2001 may be provided that is configured to be located below the sealing surface 216 of the fluidic connector 110. In some embodiments the reinforcement 2001 may comprise a layer or skirt of flexible film, comprising at least one centrally located aperture 2002. The reinforcement may comprise any suitable shape, such as an annular or circular ring. Likewise, the at least one aperture may comprise a shape that is not circular, or may comprise a plurality of apertures, as long as fluid communication between the at least one aperture 229 in the sealing surface 216 and the wound dressing 100 is not interrupted when in use. For example, in some embodiments the reinforcement 2001 may comprise a substantially circular skirt with an outer diameter that is larger than the distal end of the fluidic connector 110, for example about 40 mm. The aperture 2002 of the reinforcement 2001 may be substantially circular and have a diameter that is substantially the same as the at least one aperture 229 (corresponding to 541 in FIG. 5C) of the sealing surface 216 of the fluidic connector 110 and the orifice 227 in the backing layer of the wound dressing 100, for example 10 mm. In other embodiments the aperture 2002 may be larger than the orifice 227 in the backing layer of the wound dressing. The aperture 2002 of the reinforcement 2001 may be larger than the aperture 229 in the sealing surface 216 of the fluidic connector; however in other embodiments the inner diameter may be smaller than the aperture 229 in the sealing surface 216 of the fluidic connector.

The reinforcement 2001 may comprise any suitable high strength non-porous flexible film, tape or fabric such that when adhered to the wound dressing 100, the fluidic connector 110 is able to withstand a pull force of about 15N without creating pinholes in the top layer of the wound dressing 100. The reinforcement 2001 may comprise PU, PET, Nylon, or PVCI. The reinforcement 2001 may comprise PE or PP where an appropriate adhesive is used with the reinforcement.

The reinforcement 2001 may further comprise an adhesive on the lower, wound-facing surface for use in sealing the reinforcement to a wound dressing. The adhesive may be, for example a pressure sensitive adhesive, or a UV curable adhesive such as Loctite 4011-SG adhesive. In certain embodiments the relative stiffness of the reinforcement 2001 compared to the top layer of the wound dressing 100 may allow for an even coating of adhesive to be applied to the reinforcement. An even coating of adhesive may not comprise sharp outcrop or peaks. The adhesive coating may cover substantially the entire lower surface of the reinforcement 2001.

As shown in FIG. 20B, in certain embodiments the skirt 2001 may additionally provide a substantially flat area to apply an adhesive to thereby adhere the skirt 2001 to the top surface of the wound dressing 100. In some embodiments the bottom, wound-facing surface of a fluidic connector may comprise ridges, or raised portions which may lead to the formation of peaks or outrunners of adhesive when an adhesive applied to the bottom surface of the fluidic connector is used to adhered the fluidic connector to the top surface of a wound dressing 100. By providing a substantially flat surface on which to apply adhesive, adhering the skirt 2001 to the top surface of a wound dressing 100 may not lead to the formation of peaks or outrunners of adhesive. Further, the material properties of the reinforcement 2001 as compared to the top surface of the wound dressing 100 reduce the risk of pinholing due to pull forces on the fluidic connector when the bottom surface of the fluidic connector is adhered to the reinforcement 2001.

In other embodiments, a separate adhesive or glue layer may be applied to either the wound dressing 100 or the reinforcement 2001 prior to adhering the reinforcement 2001 to the wound dressing 100. Further, the sealing surface 216 of the fluidic connector 110 may also comprise an adhesive for use in adhering the sealing surface 216 of the fluidic connector 110 to the reinforcement 2001 and optionally the wound dressing 2010.

Figure 20C:
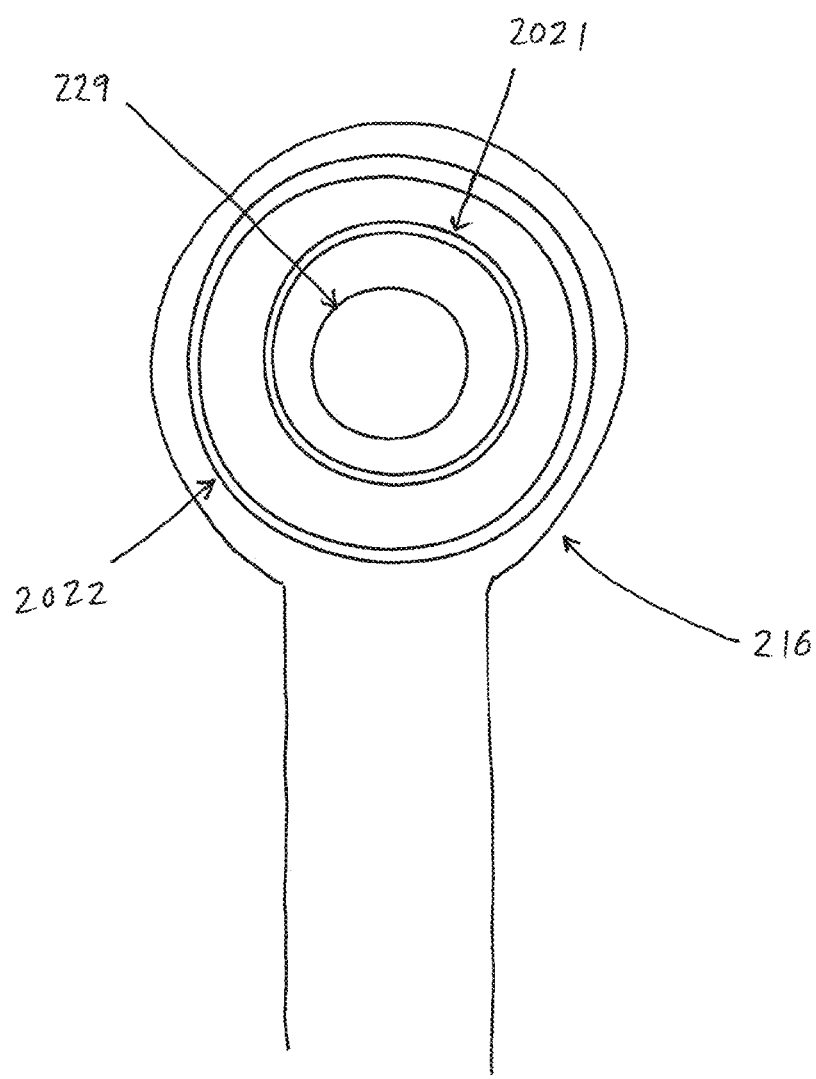
FIG. 20C illustrates a bottom view of an embodiment of flexible fluidic connector.

As shown in FIG. 20C, the lower surface of the sealing layer 216 may comprise at least one aperture 229 therein to communicate with the wound dressing 100. In some embodiments the aperture 229 may be substantially the same dimensions as an aperture in the top surface of the wound dressing 100. In some embodiments the aperture may be, for example 10 mm. The lower surface of the sealing surface 216 may comprise one or more adhesive layers or rings to adhere the sealing surface to the reinforcement 2001 and optionally the wound dressing 100. The sealing surface 216 may in some cases be protected by an optional release layer to be removed prior to use. In some embodiments the sealing surface 216 may comprise a first adhesive 2021, such as in the shape of a ring, which surrounds an aperture 229 in the sealing surface 216. A second adhesive 2022, such as in the shape of a ring, may also surround an aperture 229 in the sealing surface 216, adjacent to and spaced apart from the first adhesive 2021. In some embodiments the first adhesive and the second adhesive may be the same adhesive. In some other embodiments the first adhesive and second adhesive may be different adhesives. The adhesive or adhesives of the first adhesive layer 2021 and second adhesives layer 2022 may be separate adhesives from the adhesive which may be present on a lower surface of the reinforcement 2001. The first adhesive 2021 may be used to adhere the sealing surface 216 either to the top surface of the wound dressing 100, inside the aperture 2002 of reinforcement skirt 2001, or may be used to adhere the sealing surface 216 directly to the reinforcement skirt 2001. The second adhesive 2022 may be used to adhere the sealing surface to the reinforcement skirt.

In certain embodiments the reinforcement skirt 2001 is adhered to the sealing surface 216 by a first ring of adhesive that is smaller than a second, larger ring of adhesive which may be applied to the wound-facing surface of the skirt 2001 and is used to adhere the skirt 2001 to the backing layer of the wound dressing 100. Because the spacer 520 may cause the lower layer 540 of the fluidic connector to not be perfectly flat, this first ring of adhesive between the sealing surface and the reinforcement skirt may be positioned directly below the enlarged end of the spacer element 520, while the second, larger ring of adhesive between the skirt and the wound dressing may be positioned beyond the enlarged end of the spacer element.

Figure 20D:
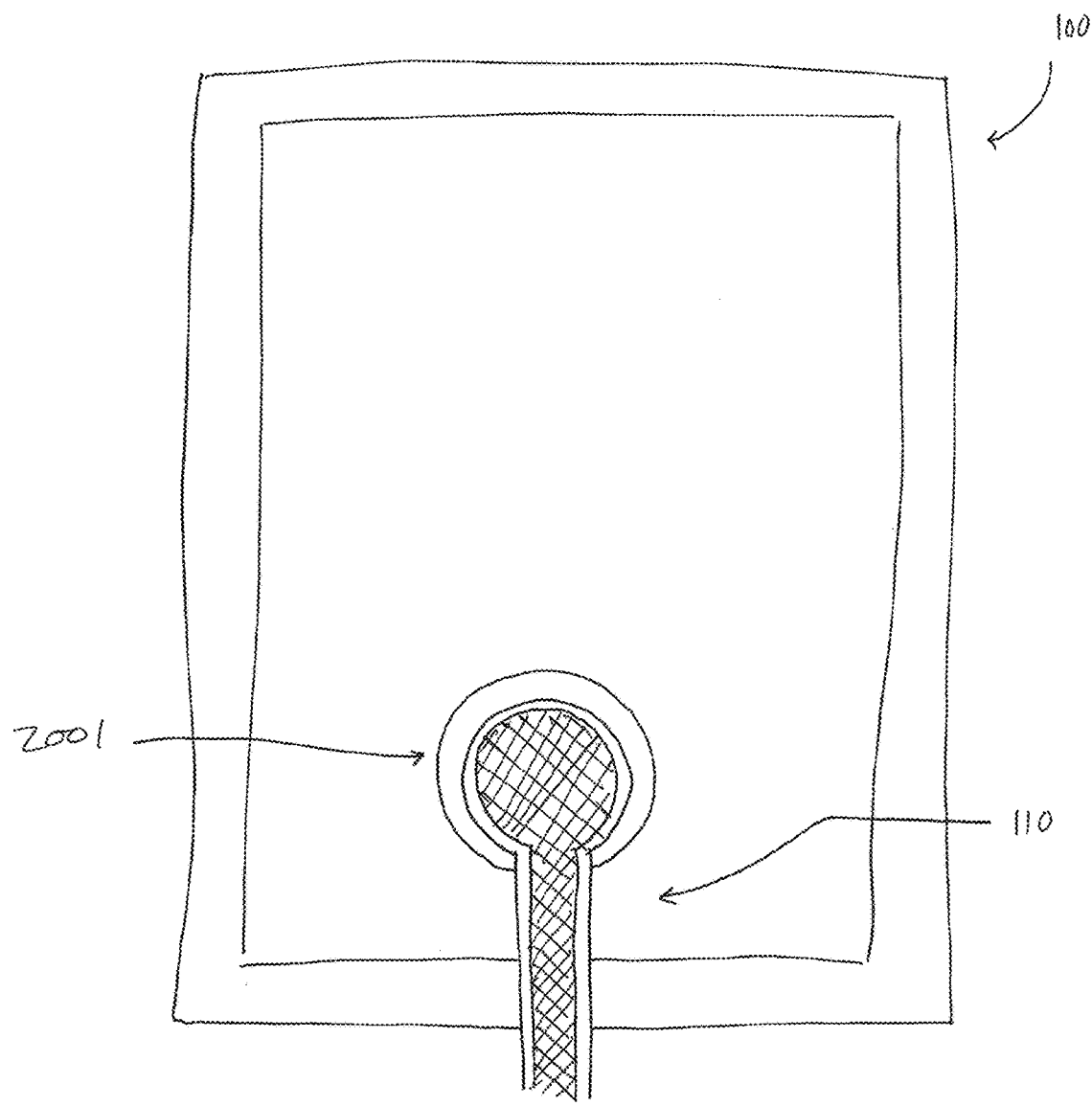
FIG. 20D illustrates a top view of a negative pressure wound treatment system employing a wound dressing and a fluidic connector with a reinforcement.

As depicted in FIG. 20D, the reinforcement 2001 (shown here as being circular as opposed to the partly elongated shape of FIG. 20A) is adhered to the top layer of a wound dressing 100 as described above. The reinforcement 2001 may be adhered to the wound dressing 100 so that the aperture 2002 in the reinforcement 2001 is placed over and is in communication with the orifice 227 in the top surface of the wound dressing. In some alternative embodiments, the reinforcement may be adhered to the sealing surface 216 of the fluidic connector 110, surrounding an aperture 229 therein, prior to adhering the reinforcement 2001 to the wound dressing 100. In some embodiments the sealing surface 216 and the reinforcement 2001 are provided as an integral unit.

With reference again to FIG. 20D, the fluidic connector 110 is positioned such that the one or more adhesive rings on the sealing surface 216 surround an orifice 227 in the wound dressing and an aperture in the reinforcement skirt 2001. In some embodiments, where the fluidic connector 110 is adhered to the reinforcement 2001 and the wound dressing 100, the first adhesive layer 2021 may act to form a seal between the sealing surface 216 and the top surface of the wound dressing 100, while the second adhesive layer 2022 may act so secure the sealing surface 216 to the reinforcement 2001. In other embodiments the one or more rings or layers of adhesive on the sealing surface 216 may adhere to and seal with the reinforcement skirt, and not the cover layer of the wound dressing 100. Thereafter, the fluidic connector 2000 may be connected to a source of negative pressure to communicate negative pressure through the fluidic connector 2000 to the wound site via the wound dressing 2010 as previously described herein.

The reinforcement 2001 as described above may serve to more evenly distribute the stresses applied to the top layer of a wound dressing when a fluidic connector adhered thereto is pulled away from the dressing. Rather than focusing areas of intense stress at localized peaks of adhesive, the reinforcement applies the pulling stress to a larger area of the top layer of the dressing. By distributing the pulling load over a larger area of the top layer, the risk of pin holing in the dressing after a small tug is greatly reduced.

Figure 21:
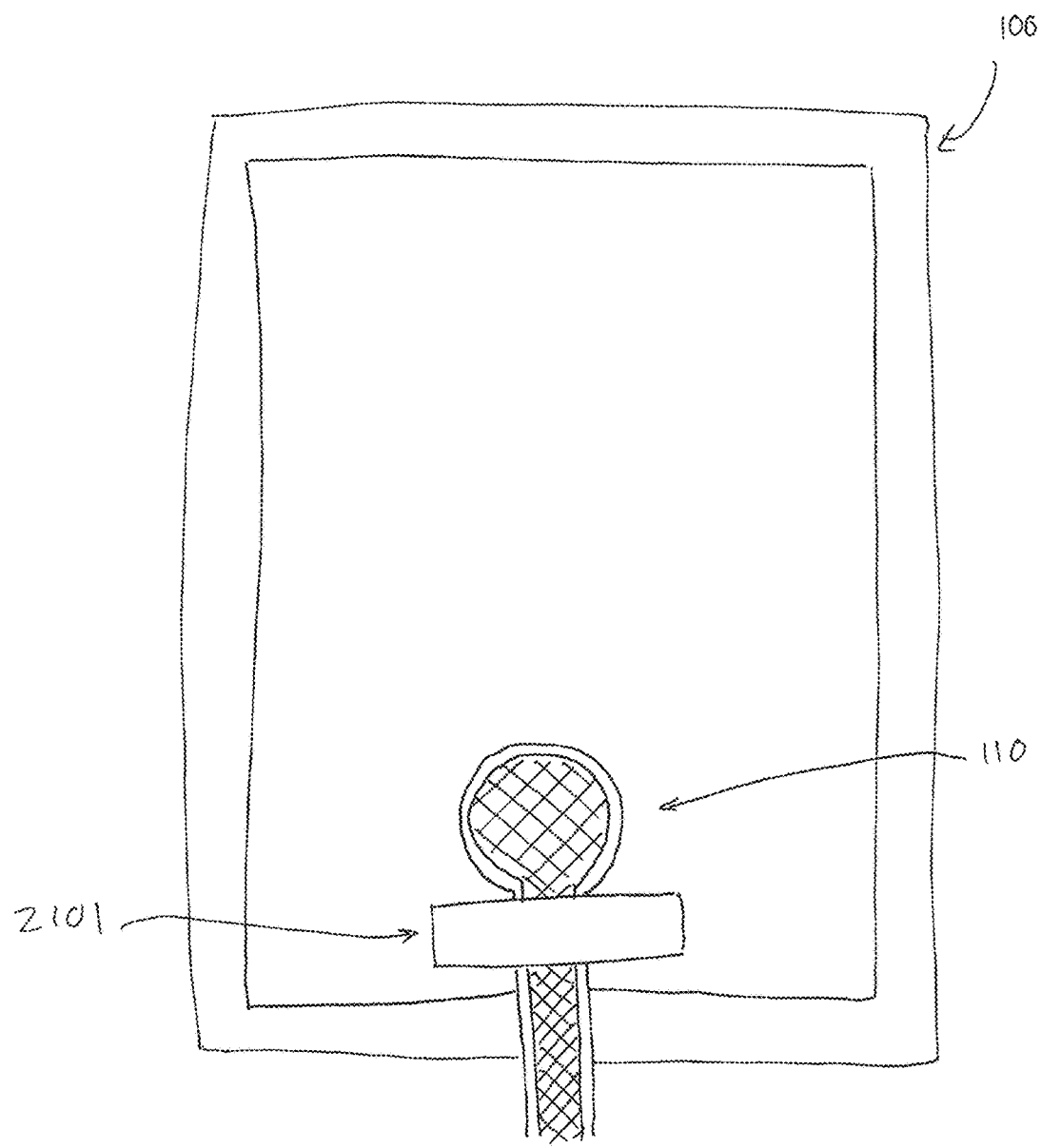
FIG. 21 illustrates a top view of a negative pressure wound treatment system employing a wound dressing and a fluidic connector with a reinforcement

FIG. 21 illustrates another embodiment of a reinforcement. A fluidic connector 110 may be similar to the fluidic connectors described above with respect to FIGS. 1-20. A reinforcement 2101 may be located over the top layer of the fluidic connector 110. In some embodiments the reinforcement 2101 comprises a strip or portion of adhesive tape. Although the reinforcement is depicted as rectangular, the reinforcement may comprise other shapes.

The reinforcement 2101 may comprise any suitable high strength flexible film, tape or fabric such that when adhered to the wound dressing 100, the fluidic connector 110 is able to withstand a pull force of about 15N without creating pinholes in the top layer of the wound dressing 100. The reinforcement 2101 may comprise PU, PET, Nylon, or PVCI. The reinforcement 2101 may comprise PE or PP where an appropriate adhesive is used with the reinforcement. The reinforcement may comprise a polymer film or a woven or non-woven fabric material.

The reinforcement 2101 may further comprise an adhesive on the lower, wound-facing surface for use in sealing the reinforcement to a wound dressing. The adhesive may be, for example a pressure sensitive adhesive, or a UV curable adhesive such as Loctite 4011-SG adhesive. In certain embodiments the relative stiffness of the reinforcement 2101 compared to the top layer of the wound dressing 2110 may allow for an even coating of adhesive to be applied to the reinforcement. An even coating of adhesive may not comprise sharp outcrop or peaks. The adhesive coating may cover substantially the entire lower surface of the reinforcement 2101. Further, the sealing surface of the fluidic connector 2100 may also comprise an adhesive for use in sealing the sealing surface of fluidic connector to the wound dressing 2110 over an orifice therein. In some embodiments the adhesive on the lower surface of the reinforcement 2101 may be the same as the adhesive on the sealing surface 216 of the fluidic connector 110. In some embodiments separate adhesives may be used.

In use, as depicted in FIG. 21, the fluidic connector 110 is adhered to the top layer of a wound dressing 100 as described above. The fluidic connector 110 may be adhered to the top layer of the wound dressing over an orifice 227 therein. The reinforcement 2101 may be adhered to the top layer of the fluidic connector substantially adjacent to an orifice in the top layer of the wound dressing 100. For example, the reinforcement may be positioned overlying the absorbent layer along an edge of the wound dressing 100. The reinforcement may, for example, be adhered to the fluidic connector 110 between the proximal end and the applicator. In some embodiments the top layer of the fluidic connector 208 and the reinforcement 2101 are provided as an integral unit. Thereafter, the fluidic connector 110 may be connected to a source of negative pressure to communicate negative pressure through the fluidic connector 110 to the wound site via the wound dressing 100 as previously described herein.

The reinforcement 2101 as described above may serve to more evenly distribute the stresses applied to the top layer of a wound dressing when a fluidic connector adhered thereto is pulled away from the dressing. Rather than focusing areas of intense stress at localized peaks of adhesive, the reinforcement applies the pulling stress to a larger area of the top layer of the dressing. By distributing the pulling load over a larger area of the top layer, the risk of pin holing in the dressing after a small tug is greatly reduced.

In some other embodiments, the reinforcement may extend over the entire distal end of the applicator. The reinforcement may comprise a film layer or section of adhesive tape, for example a PU, PET, Nylon, or PVCl patch. In some embodiments the reinforcement may be rectangular, although it may be any other suitable shape. The reinforcement may be transparent. The reinforcement comprises an adhesive on the lower, wound-facing surface for use in sealing the reinforcement to the top surface of the top layer of the wound dressing and the top surface of the fluidic connector. In use, a fluidic connector, as described herein above, is adhered to the top layer of a wound dressing, which may be similar to the wound dressing 10 as described in International Patent Publication WO2013175306, which is hereby incorporated by reference in its entirety. The fluidic connector may be adhered to the top layer of the wound dressing over an orifice therein. The reinforcement may be adhered to the top surface of the fluidic connector and to the top surface of the top layer of the wound dressing. The reinforcement is sufficiently large so as to extend past the edges of the distal end of the fluidic connector to seal with the top layer of the wound dressing.

Figure 22:
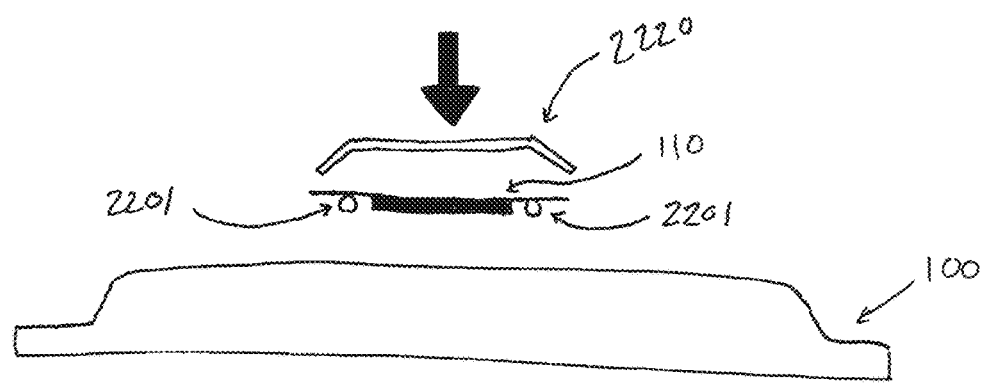
FIG. 22 illustrates an embodiment of a tapered compression plate for use in adhering a fluid connector to a wound dressing.

Turning now to FIG. 22, in some embodiments, a fluidic connector may be adhered to the top surface of a wound dressing via an applicator, as described herein above. The fluidic connector may be similar to the fluidic connectors described above with respect to FIGS. 1-21. The applicator may be adhered to the cover layer of the dressing by an adhesive, such as an adhesive ring or bead. As depicted in FIG. 22, in some embodiments a tapered compression plate may be used to form a substantially uniform adhesive bead.

As shown in FIG. 22, the compression plate may comprise a substantially flat central portion 2221 and a tapered outer edge 2222. In some embodiments the compression plate 2220 may have a substantially circular shape, although it will be appreciated that any suitable shape may be used. As described above, the fluidic connector 110 may comprise an adhesive ring or bead 2201. In some embodiments, the adhesive may be located on the sealing surface of the fluidic connector, surrounding an aperture in the sealing surface. The fluidic connector may be adhered to the top layer of the wound dressing 100 over an orifice therein.

In use, the compression plate presses the fluidic connector 110 to the top surface of the dressing 100 to thereby exert a compressive force on the adhesive bead 2201. The compressive force exerted by the compression plate 2220 causes the adhesive to flow perpendicularly to the axis of compression. As the adhesive flows outwardly, towards the edge of the compression plate 2220, the tapered outer edge 2222 prevents the adhesive from flowing past itself. In this manner, the tapered outer edge 2222 may act as a terminus for the flowing adhesive 2201 and thereby create a circular ring of adhesive. Thereafter the compression plate 2220 may cease to press the fluidic connector 2200 to the top surface of the dressing 100 and the adhesive may be cured. It will be appreciated that in some embodiments the adhesive may be cured, or begin to be cured before the compressive plate ceases to press the fluidic connector 110 to the top surface of the dressing 100.

The circular adhesive ring formed by the compression plate comprises a substantially uniform outer edge, and does not comprise localized peaks of adhesive. Therefore, when a fluidic connector or suction port adhered to a top surface of a wound dressing is pulled away from the dressing there are no localized peaks of adhesive to create areas of intense stress concentration, reducing the risk of pin holing in the dressing after a small tug.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A wound treatment apparatus comprising:
a wound dressing comprising a cover layer and an absorbent layer for absorbing wound exudate positioned beneath the cover layer, wherein the absorbent layer comprises a super-absorbent material and defines a smaller perimeter than the cover layer, such that a boundary region of the cover layer surrounding the absorbent layer is defined between an edge of the absorbent layer and an edge of the cover layer, and wherein the wound dressing is configured to substantially retain the wound exudate within the wound dressing when negative pressure is provided to the wound dressing;
a fluidic connector configured to provide negative pressure to the wound dressing through an aperture in the cover layer, the aperture in the cover layer being located over the absorbent layer, the fluidic connector comprising:
    a spacer layer comprising a proximal end, an elongate middle portion and a distal end;
    a top layer constructed from a liquid impermeable material provided over the spacer layer;
    a bottom layer constructed from a liquid impermeable material provided below the spacer layer, wherein the top layer and the bottom layer substantially enclose the spacer layer, and wherein the top layer and the bottom layer have enlarged distal ends surrounding the distal end of the spacer layer;
    a sealing surface on a lower surface of the bottom layer for sealing the fluidic connector to a top surface of the cover layer, the sealing surface comprising an opening positioned over the aperture in the cover layer; and
    an elongate conduit extending away from the sealing surface defined between the top layer and the bottom layer; and
a reinforcement directly adhered to both the fluidic connector and a top surface of the cover layer and configured to provide additional securement between the fluidic connector and the cover layer, the reinforcement comprising:
    an upper surface;
    a lower, wound-facing surface; and
    an adhesive disposed on the wound-facing surface of the reinforcement, wherein the adhesive is configured to seal the reinforcement to the top surface of the cover layer,
wherein the reinforcement is positioned along at least a portion of the fluidic connector between the opening in the cover layer above the absorbent layer and the boundary region of the cover layer,
wherein the reinforcement is positioned only above the absorbent layer and is not positioned over the boundary region of the cover layer, and
wherein the wound dressing comprising the cover layer and the absorbent layer, the fluidic connector, and the reinforcement are adhered together to form a single unit for simultaneous positioning and removal of the wound dressing, the fluidic connector and the reinforcement to and from a wound site.

2. The wound treatment apparatus of claim 1, wherein the reinforcement is configured to be positioned between the top surface of the cover layer and the lower surface of the bottom layer, wherein the lower surface of the bottom layer is configured to be adhered to the reinforcement.

3. The wound treatment apparatus of claim 2, wherein the reinforcement is positioned between the top surface of the cover layer and the lower surface of the bottom layer.

4. The wound treatment apparatus of claim 2, wherein the reinforcement comprises a strip of adhesive tape.

5. The wound treatment apparatus of claim 4, wherein the strip of adhesive tape is adhered to configured to be positioned between the sealing surface and the edge of the cover layer.

6. The wound treatment apparatus of claim 2, wherein the reinforcement comprises a skirt configured to be positioned between the sealing surface and the top surface of the cover layer, the skirt comprises an opening configured to be positioned over the aperture in the cover layer.

7. The wound treatment apparatus of claim 2, wherein the sealing surface is adhered to the top surface of the cover layer with a first adhesive, and the lower surface of the bottom layer of the fluidic connector is adhered to the reinforcement with a second adhesive.

8. The wound treatment apparatus of claim 7, wherein the first adhesive is an adhesive ring that surrounds the aperture in the cover layer, and the second adhesive is one of a second adhesive ring surrounding the first adhesive ring and an adhesive layer on a lower surface of the elongate conduit.

9. The wound treatment apparatus of claim 1, wherein the reinforcement is provided over the fluidic connector.

10. The wound treatment apparatus of claim 9, wherein the reinforcement provided over the fluidic connector is an adhesive tape provided over the elongate conduit and adhered to the top surface of the cover layer on opposite sides of the elongate conduit.

11. The wound treatment apparatus of claim 9, wherein the reinforcement is transparent.

12. The wound treatment apparatus of claim 1, wherein the sealing surface is provided at an enlarged distal end of the fluidic connector.

13. The wound treatment apparatus of claim 1, wherein the fluidic connector further comprises one or more apertures in the bottom layer beneath the distal end of the spacer layer.

14. The wound treatment apparatus of claim 13, wherein the spacer layer comprises a 3D fabric material.

15. The wound treatment apparatus of claim 1, wherein the fluidic connector further comprises a filter positioned across the opening in the sealing surface.

16. The wound treatment apparatus of claim 1, wherein the wound dressing further comprises a wound contact layer, wherein the absorbent layer is positioned between the wound contact layer and the cover layer.

17. The wound treatment apparatus of claim 16, wherein the wound dressing further comprises one or more transmission layers between the wound contact layer and the cover layer.

18. The wound treatment apparatus of claim 17, wherein the one or more transmission layers comprise 3D fabric material.

19. The wound treatment apparatus of claim 17, comprising a transmission layer beneath the absorbent layer.

20. The apparatus of claim 1, further comprising a vacuum source configured to apply negative pressure to the wound site to the fluidic connector and through the wound dressing, wherein the wound dressing and the fluidic connector are configured to be directly or indirectly connected to the vacuum source and configured to apply negative pressure from the vacuum source without positioning a collection canister configured to collect fluid between the fluidic connector and the vacuum source.

21. The apparatus of claim 1, wherein the reinforcement is constructed of a single layer having a partly elongated teardrop shape sized to substantially span the entirety of the sealing surface.

22. A wound treatment apparatus comprising:
a wound dressing comprising:
a cover layer comprising an aperture;
a wound contact layer; and
an absorbent layer between the cover layer and the wound contact layer, wherein the absorbent layer comprises a super-absorbent material;
a reinforcement layer directly adhered to a top surface of the cover layer above the absorbent layer, wherein the reinforcement layer comprises:
an opening positioned above the aperture in the cover layer; and
an adhesive disposed on a lower, wound-facing surface of the reinforcement layer, wherein the adhesive seals the lower surface of the reinforcement layer to the top surface of the cover layer;
a fluidic connector configured to provide negative pressure to the wound dressing through the aperture in the cover layer, the fluidic connector comprising:
a sealing surface directly adhered to an upper surface of the reinforcement layer, wherein the sealing surface surrounds the opening in the reinforcement layer;
an upper surface positioned above the sealing surface that defines a vertical height between the sealing surface and the upper surface; and
an elongate conduit extending laterally away from the aperture in the cover layer and the opening in the reinforcement layer, the elongate conduit extending generally parallel to the top surface of the cover layer; and
a filter positioned beneath the upper surface of the fluidic connector, the filter configured to substantially prevent wound exudate from entering the elongate conduit and to retain wound exudate within the absorbent layer during application of negative pressure to the wound dressing, wherein the filter is sized to span the aperture in the cover layer.

23. The wound treatment apparatus of claim 22, wherein the filter is positioned between the sealing surface and the upper surface of the fluidic connector.

24. The wound treatment apparatus of claim 22, wherein the filter is positioned between the upper surface of the fluidic connector and the cover layer.

25. The wound treatment apparatus of claim 22, wherein the filter is positioned between the reinforcement layer and the cover layer.

26. The wound treatment apparatus of claim 22, wherein the filter is positioned between the reinforcement layer and the upper surface of the fluidic connector.

27. The wound treatment apparatus of claim 22, wherein the sealing surface is provided on a lower layer of the fluidic connector, the lower layer comprising an opening that is positioned over the opening in the reinforcement layer, and the upper surface is provided on an upper layer of the fluidic connector, wherein the upper and lower layers are adhered together.

28. The wound treatment apparatus of claim 27, further comprising a spacer layer between the upper and lower layers.

29. The wound treatment apparatus of claim 28, wherein the elongate conduit comprises elongated portions of the upper layer, the spacer layer and the lower layer.

30. The wound treatment apparatus of claim 28, wherein the filter is located between the spacer layer and the lower layer.

31. The wound treatment apparatus of claim 22, wherein the reinforcement layer has an outer perimeter larger than an outer perimeter of the sealing surface.

32. The wound treatment apparatus of claim 31, wherein the reinforcement layer comprises a generally circular ring.

33. The wound treatment apparatus of claim 22, wherein a first adhesive ring surrounding the opening in the reinforcement layer and surrounding the aperture in the cover layer adheres the lower surface of the reinforcement layer to the cover layer, and a second adhesive ring surrounding the opening in the reinforcement layer adheres the sealing surface to the upper surface of the reinforcement layer.

34. The wound treatment apparatus of claim 33, wherein the first adhesive ring has a larger diameter than the second adhesive ring.

35. The wound treatment apparatus of claim 22, wherein adhesive adheres the sealing surface of the fluidic connector to both the reinforcement layer and to the top surface of the cover layer.

36. The apparatus of claim 22, wherein the wound dressing comprising the cover layer, the wound contact layer and the absorbent layer, the fluidic connector, and the reinforcement layer are adhered together to form a single unit for simultaneous positioning and removal of the wound dressing, the fluidic connector and the reinforcement layer to and from a wound site.

37. The apparatus of claim 22, wherein the reinforcement layer is constructed of a single layer having a partly elongated teardrop shape sized to substantially span the entirety of the sealing surface.

38. An apparatus for providing negative pressure to a wound, the apparatus comprising:
a fluidic connector configured to provide negative pressure to a wound dressing through an aperture in a cover layer of the wound dressing, the fluidic connector comprising:
a sealing surface on a lower surface of the fluidic connector;

an upper surface positioned above the sealing surface that defines a vertical height between the sealing surface and the upper surface; and an elongate conduit extending away from sealing surface;

wherein the fluidic connector comprises an enlarged distal end configured to be in fluid communication with the wound dressing and wherein the sealing surface of the fluidic connector is provided at the enlarged distal end of the fluidic connector;

a reinforcement layer configured to be adhered to a top surface of the wound dressing, wherein the reinforcement layer comprises an opening configured to be positioned above the aperture in the cover layer, and a filter positioned beneath the upper surface of the fluidic connector and between the sealing surface and the reinforcement layer, wherein the filter is sized to substantially span the opening in the reinforcement layer;

wherein the sealing surface is configured to be adhered to the reinforcement layer and surround the opening in the reinforcement layer;

wherein the reinforcement layer is constructed of a single layer having a partly elongated teardrop shape sized to substantially span the entirety of the sealing surface.

39. The apparatus of claim 38, wherein the reinforcement layer comprises a skirt of flexible film.

40. The apparatus of claim 38, wherein the reinforcement layer comprises polypropylene and further comprises an adhesive on a lower, wound-facing surface for use in sealing the reinforcement layer to the wound dressing.

41. The apparatus of claim 38, wherein the fluidic connector comprises:

a spacer layer comprising a proximal end, an elongate middle portion and a distal end;

a top layer constructed from a liquid impermeable material provided over the spacer layer;

a bottom layer constructed from a liquid impermeable material provided below the spacer layer, wherein the top layer and the bottom layer substantially enclose the spacer layer; and one or more apertures in the bottom layer beneath the distal end of the spacer layer.

42. The apparatus of claim 38, further comprising a first adhesive ring surrounding the opening in the reinforcement layer and configured to surround the aperture in the cover layer to adhere the reinforcement layer to the cover layer, and a second adhesive ring surrounding the opening in the reinforcement layer configured to adhere the sealing surface to the reinforcement layer.

* * * * *